United States Patent [19]

Gage et al.

[11] Patent Number: 5,082,670

[45] Date of Patent: Jan. 21, 1992

[54] METHOD OF GRAFTING GENETICALLY MODIFIED CELLS TO TREAT DEFECTS, DISEASE OR DAMAGE OR THE CENTRAL NERVOUS SYSTEM

[75] Inventors: Fred H. Gage, La Jolla; Michael B. Rosenberg, San Diego; Theodore Friedmann, La Jolla, all of Calif.

[73] Assignee: The Regents of the University of California, Oakland, Calif.

[21] Appl. No.: 285,196

[22] Filed: Dec. 15, 1988

[51] Int. Cl.$^5$ .................. A61K 35/00; A61K 48/00; C12N 15/00

[52] U.S. Cl. .................. 424/520; 424/570; 435/172.3; 435/240.2; 435/948; 935/62; 935/70; 514/44

[58] Field of Search .................. 424/95, 520, 570; 435/172.3, 948, 69.1, 317.1; 935/62, 70; 800/DIG. 2; 514/44

[56] References Cited

U.S. PATENT DOCUMENTS 4,497,796 2/1985 Salser et al. .................. 424/95

OTHER PUBLICATIONS

Gape et al. (a), Neuroscience 22 (Suppl.): S590 (1987).
Gape et al. (b), Neuroscience 23: 795-807 (1987).
Selden et al. Science 236: 714-718 (1987).
Ernfors et al. Proc. Natl. Acad. Sci. 86: 4756-4760 (1989).
Short et al., Soc. Neurosci. Abst. 14(2): 1115 (1988).
Fieldmann et al., J. Cell. Biochem. Suppl. 0 (12 Part B).
Breakefield et al., J. Cell. Biochem. Suppl. 0 (12 Part B): 170 (1988).
Rosenstein, J. M., "Neocortical Transplants in the Mammalian Brain Lack a Blood-Brain Barrier to Macromolecules," Science 235:772-774 (1987).
Bjorklund et al., Neural Grafting in the Mammalian CNS, Ch. 3-8, Elsevier, Amsterdam (1985).
Sladek et al., Neural Transplants: Development and Function, Plenum Press, New York (1984).
Marsden, "Movement Disorders and the Basal Ganglia," Trends Neurasci 9:512 (1986).
Vinken et al., Eds., "Drug-Induced Movement Disorders (Tardive Dyskinesia and Dopa-Induced Dyskinesia)," Handbook of Clinical Neurology, (Tanner, Author), pp. 185-204, Elsevier, Amsterdam (1986); vol. 5.
Backlund et al., "Transplantation of Adrenal Medullary Tissue to Striatum in Parkinsonism," J. Neurosurg. 62:169-173 (1985).
Madrazo et al., "Open Microsurgical Autograft of Adrenal Medulla to the Right Caudate Nucleus in Two Patients with Intractable Parkinson's Disease," New Eng. J. Med. 316:831-834 (1987).
Bjorklund et al., "Neural Grafting in Animal Models of Neurodegenerative Diseases," Ann. N.Y. Acad. Sci. 457-53-81 (1986).
Dunnett et al., "Dopamine-Rich Transplants in Experimental Parkinsonism," Trends Neurosci 6:266-270 (1983).
Gusella et al., "A Polymorphic DNA Marker Genetically Linked to Huntington's Disease," Nature 306:234-238 (1983).
Delabar et al., "B Amyloid Gene Duplication in Alzheimer's Disease and Karyotypically Normal Down Syndrome," Science New York, 235:1390-1392 (1987).
Goldgaber et al., "Characterization and Chromosomal Localization of a cDNA Encoding Brain Amyloid of Alzheimer's Disease," Science N.Y., 235, 877-880 (1987).
St. George-Hyslop et al., "The Genetic Defect Causing Familia Disease Maps on Chromosome 21," Science N.Y. 235:885-890 (1987).

(List continued on next page.)

Primary Examiner—Elizabeth C. Weimar
Assistant Examiner—Jasemine C. Chambers
Attorney, Agent, or Firm—SaraLynn, Mandel, Sheldon & Mak

[57] ABSTRACT

Methods of genetically modifying donor cells by gene transfer for grafting into the central nervous system to treat diseased or damaged cells are disclosed. The modified donor cells produce a molecule capable of affecting the recovery of cells in the CNS. Methods and vectors for carrying out gene transfer and grafting are described.

27 Claims, 22 Drawing Sheets

OTHER PUBLICATIONS

Tanzi et al., "Amyloid B Protein Gene: cDNA, m RNA Distribution", and Genetic *Science N.Y.* 235:880–884 (1987).

Baron et al., "Genetic Linkage Between X--Chromosome Markers and Bipolar Affective Illness," *Nature* 326:289–292 (1987).

Sherrington et al. "Localization of a Susceptibility Locus for Schizophrenia on Chromosome 5," *Nature* 336:164–167 (1988).

Anderson, "Prospects for Human Gene Theraphy," *Science* 226:401–409 (1984).

Friedmann et al., "Gene Therapy for Human Genetic Disease"? *Science* 175:949–955 (1972).

Friedmann, *Gene Therapy: Fact and Fiction in Biology's New Approaches to Disease*, Cold Spring Harbor Laboratory, New York (1983).

Constantini et al., "Correction of Murine B-Thalassemia by Gene Transfer into the Germ Line," *Science* 233:1192–1194 (1986).

Mason et al., "The Hypogonadal Mouse: Reproductive Functions Restored by Gene Therapy," *Science,* 234:1372–1378 (1986).

Readhead et al., "Expression of a Myelin Basic Protein Gene in Transgenic Shiverer Mice: Correction of the Dysmyelinating Phenotype," *Cell* 48:703–712 (1987).

Gilboa et al., "Transfer and Expression of Cloned Genes Using Retroviral Vectors," *BioTechniques* 4:504–512 (1986).

Shimotohno et al., "Formation of Infectious Progeny Virus After Insertion of Herpes Simplex Thymidine Kinase Gene into DNA of an Avian Retrovirus," *Cell* 26:67–77 (1981).

Wei et al., "Construction and Isolation of a Transmissible Retrovirus Containing the scr Gene of Harvey Murine Sarcoma Virus and the Thymidine Kinase Gene of Herpes Simplex Virus Type I," *J. Virol.* 39:935–944 (1981).

Tabin et al., "Adaptation of a Retrovirus as a Eucaryotic Vector Transmitting the Herpes Simplex Virus Thymidine Kinase Gene," *Cell Biol.* 2:426–436 (1982).

Kantoff et al., "Correction of Adenosine Deaminase Deficiency in Cultured Human T and B Cells by Retrovirus-Mediated Gene Transfer," *Proc. Natl. Acad. Sci. USA* 83:6563–6567 (1986).

Willis et al., "Partial Phenotypic Correction of Human Lesch-Nyhan (Hypoxanthine-Guanine Phosphoriboxyltransferase-Deficient) Lymphoblasts with a Transmissible Retroviral Vector," *J. Biol. Chem.* 259:7842–7849 (1984).

McIvor et al., "Human Purine Nucleoside Phosphorylase and Adenosine Deaminase: Gene Transfer into Cultured Cells and Murine Hematopoietic Stem Cells by Using Recombinant Amphotropic Retroviruses", *Molec. Cell Biol.* 7:838–846 (1987).

Soriano et al., "Tissue-Specific and Ectopic Expression of Genes Introduced into Transgenic Mice by Retroviruses," *Science* 234:1409–1413 (1986).

Wolff et al., "Expression of Retrovirally Transduced Genes in Primary Cultures of Adult Rat Hepatocytes", *Proc. Natl. Acad. Sci. USA,* 84:3344–3348 (1987).

Khoury and Gruss, "Enhancer Elements", *Cell* 33:313–314 (1983).

Serfling et al., "Enhancers and Eykaryotic Gene Transcription", *Trends Genet.* 1:224–230 (1985).

Wolff and Friedmann, "Approaches to Gene Therapy in Disorders of Purine Metabolism" *Rheumatic Dis. Clin. N. Amer.* 14(2):459–477 (1988).

Eglitis and Anderson, "Retroviral Vectors for Introduction of Genes Into Mammalian Cells", *Biotechniques* 6:608–614 (1988).

Ledley, "Somatic Gene Therapy for Human Disease: Background and Prospects", *J. Pediatrics* 110:1–8 (1987).

Joyner et al., "Retrovirus Transfer of a Bacterial Gene Inot Mouse Haematopoietic Progenitor Cells", *Nature* 305: 556–558 (1983).

Miller et al., "Expression of a Retrovirus Encoding Human HPRT in Mice" *Science,* 225: 630–632 (1984).

Williams et al., "Introduction of New Genetic Material Into Pluripotent Haematopoietic Stem Cells of the Mouse" *Nature,* 310:476–480 (1984).

Selden et al., "Implantation of Genetically Engineered Fibroblasts Into Mice: Implications for Gene Therapy" *Science,* 236:714–718 (1982).

Garver et al., "Production of Glycosylated Physiologically "Normal" Human α-Antitrypsin by Mouse Fibroblasts Modified by Insertion of a Human α-Antitrypsin cDNA Using a Retroviral Vector", *Proc. Nat. Acad. Sci. USA* 84:1050–1054 (1987).

St. Louis and Verma, "An Alternative Approach to Somatic Cell Gene Therapy", *Proc. Nat. Acad. Sci. USA,* 85:3150–3154 (1988).

Morgan et al., "Expression of an Exogenous Growth Hormone Gene by Transplantable Human Epidermal Cells", *Science*, 237:1476–1479 (1987).

Geller and Breakefield, "A Defective HSV-1 Vector Expresses *Escherichia coli* β-Galactosidase in Cultured Peripheral Neurons", Science 241:1667–1669 (1988).

Lowenstein, "Junctional Intercellular Communication and the Control of Growth", *Biochem. Biophys. Actg.* 560:1–66 (1979).

Gruber et al., "Glial Cells Metabolically Cooperate: A Potential Requirement for Gene Replacement Therapy", *Proc. Natl. Acad. Sci. USA*, 82:6662–6666 (1985).

Hefti, "Nerve Growth Factor Promotes Survival of Septal Cholinergic Neurons After Fimbrial Transections", *J. Neuroscience* 6(8):2155–2162 (1986).

Williams et al., "Continuous Infusion of Nerve Growth Factor Prevents Basal Forebrain Neuronal Death After Fimbria Fornix Transection" *Proc. Natl. Acad. Sci USA* 83:9231–9235 (1986).

Korshing and Thoenen, "Nerve Growth Factor in Sympathetic Ganglia and Corresponding Target Organs of the Rat: Correlation with Density of Sympathetic Innervation", *Proc. Natl. Acad. Sci. USA* 80:3513–3516 (1983).

Whittemore et al., "Development and Regional Expression of βNerve Growth Factor Messenger RNA and Protein in the Rat Central Nervous System", *Proc. Natl. Acad. Sci. USA* 83:817–821 (1986).

Shelton and Reichardt, "Studies on the Expression of the β Nerve Growth Factor (NGF) Gene in the Central Nervous System: Level and Regional Distribution of NGF mRNA Suggest That NGF Functions as a Trophic Factor for Several Distinct Populations of Neurons", *Proc. Natl. Acad. Sci. USA* 83:2714–2718 (1986).

Larkfors et al., "Nerve Growth Factor Protein Level Increases in the Adult Rat Hippocampus After a Specific Cholinergic Lesion" *J. Neuroscience Res.* 18:525–531 (1987).

Seiler and Schwab, "Specific Retrograde Transport of Nerve Growth Factor (NGF) from Neocortex to Nucleus Basalis in the Rat", *Brain Res.* 300:33–39 (1984).

Kromer, "Nerve Growth Factor Treatment After Brain Injury Prevents Neuronal Death", *Science*, 235:214–216 (1987).

Gage et al., "Morphological Response of Axotomized Septal Neurons to Nerve Growth Factor", *J. Comp. Neurol.*, 269:147–155 (1988).

Yee et al., "Gene Expression From a Transcriptionally Disabled Retroviral Vector", *Cold Spring Harbor Symposia on Quant. Bio.*, L1:1021–1026 (1986).

Jolly et al., "High-Efficiency Gene Transfer Into Cells", *Meth. Enzymol.* 149:10–25 (1987).

Gage et al., "Retrograde Cell Changes in Medial Septum and Diagonal Band Following Fimbria-Fornix Transection: Quantitative Temporal Analysis", *Neuroscience* 19:241–255 (1986).

Gage et al., "Reinnervation of the Partially Deafferented Hippocampus by Compensatory Collateral Sprouting from Spared Cholinergic and Noradrenergic Afferent", *Brain Res.*, 268:27–37 (1983).

Rosenberg et al., "Grafting Genetically Modified Cells to the Damaged Brain: Restorative Effects of NGF Expression", *Science*, 242:1575–1578 (1988).

Wolff et al., "Grafting Fibroblasts Genetically Modified to Produce L-Dopa in a Rat Model of Parkinson Disease", *Proc. Natl. Acad. Sci. USA*, 86:9011–9014 (1989).

Rosenberg et al., "Introduction of Foreign Genes Into Adult Rat Brain Via Grafted Cells", (Abstr.), *Amer. J. Genetics*, 41:A235, Sep. (1987).

Gage et al., "Grafting of Genetically Engineered Cells to the Adult Rat Brain", (Abstr.) *Schmitt Symposium, Univ. of Rochester Med. Ctr.*, (1987).

Breakefield and Geller, "Gene Transfer Into the Nervous System", *Molecular Neurobiology*, 1:339–370 (1987).

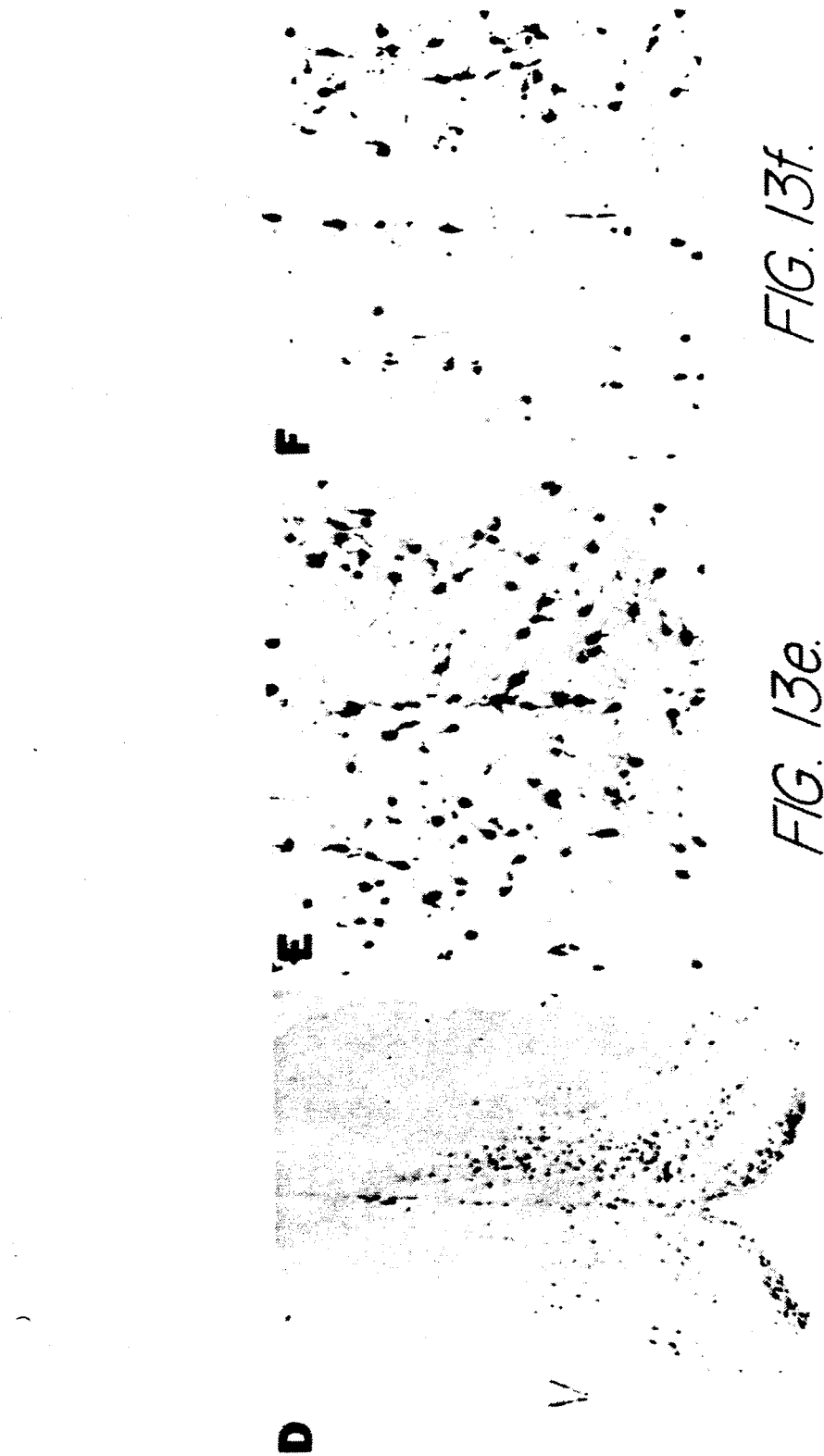

METHOD OF GRAFTING GENETICALLY MODIFIED CELLS TO TREAT DEFECTS, DISEASE OR DAMAGE OR THE CENTRAL NERVOUS SYSTEM

ACKNOWLEDGEMENT OF GOVERNMENT SUPPORT

This invention was made with Government support under Grant Contract No. NOO14-86-K-0347 awarded by the Office of Naval Research, and Grant Contract Nos. HD-20034, NIA-06088, HD-00669 awarded by NIH. The Government has certain rights in this invention.

TECHNICAL FIELD OF THE INVENTION

The present invention relates to the use of recombinant technology for genetic modification of donor cells for grafting into the central nervous system (CNS) of a subject to treat defects, disease or damage of the CNS. More specifically, the invention relates to the insertion of a gene encoding a molecule having ameliorative effects on cells including neurons into donor cells such that when the donor cells are grafted into the CNS the molecule is expressed and exerts its effects on diseased or damaged cells.

BACKGROUND OF THE INVENTION

Attempts to repair the mammalian brain or replace CNS functions resulting from defects or following disease or damage to the CNS are hampered by an incomplete understanding of the complex structure-function relationships in the CNS. Although knowledge of some basic principles of cell function in the brain has advanced greatly in recent years, understanding of interactions between clusters of cells or systems and cell circuits in different regions of the brain and their relationship to the outward manifestations of behavior and neurological function lags far behind. Difficulties in approaching these problems have been caused, in part, by the large number of different cell types in the mammalian CNS and the number and complexity of their connections. In addition, the blood-brain barrier makes access to the brain for diagnosis, treatment and the design of new therapies more difficult.

In spite of the absence of sophisticated knowledge of pathophysiology of most normal or abnormal brain functions, some attempts at pharmacological therapy for CNS dysfunction have already become useful and effective. These include the use of psycho-active drugs for psychiatric disorders such as schizophrenia, and specific replacement therapy in the rare cases in which the biochemical and cellular bases of the CNS disorder are relatively better understood, as in Parkinson's disease. At the core of most therapeutic approaches is the objective of replacing or reactivating a specific chemical function in the brain that has been lost as a consequence of disease or damage.

Intracerebral neural grafting has emerged recently as an additional potential approach to CNS therapy. The replacement or addition of cells to the CNS which are able to produce and secrete therapeutically useful metabolites may offer the advantage of averting repeated drug administration while also avoiding the drug delivery complications posed by the blood-brain barrier. (Rosenstein, *Science* 235:772-774 (1987)). While the concepts and basic procedures of intracerebral grafting have been known for decades, most of the factors that optimize the survival of grafted cells have only recently come to be investigated and partially understood. (Bjorklund et al., in *Neural Graftinc in the Mammalian CNS*, p. 709, Elsevier, Amsterdam (1985); Sladek et al., in *Neural Transplants: Development and Function*, Plenum Press, N.Y. (1984)). Several factors critical for reliable and effective graft survival have been identified, including the following:

(1) Age of the donor: efficiency of grafting is reduced with increasing age of donor cells.

(2) Age of the host: young recipients accept grafts more readily than older ones.

(3) Availability of neuronotrophic factors in the host and donor tissue: wound-induced neurotrophic factors enhance graft survival.

(4) Immunological response: the brain is not totally an immunologically privileged site.

(5) The importance of target-donor matching: neurons survive better when they are grafted to a site which they would normally innervate.

(6) Vascularization: it is critical that the grafts be vascularized rapidly or otherwise sufficiently well nourished from the environment.

As these critical factors have become recognized and optimized, intracerebral grafting has become a valid and reliable tool for neurobiologists in the study of CNS function and potentially for clinicians for the design of therapies of CNS disease. This approach has reached a level of experimental clinical application in Parkinson's disease.

Parkinson's disease is an age-related disorder characterized by a loss of dopamine neurons in the substantianigra of the midbrain, which have the basal ganglia as their major target organ. The symptoms include tremor, rigidity and ataxia. The disease is progressive but can be treated by replacement of dopamine through the administration of pharmacological doses of the precursor for dopamine, L-DOPA, (Marsden, *Trends Neurosci.* 9:512 (1986); Vinken et al., in *Handbook of Clinical Neurology* p. 185, Elsevier, Amsterdam (1986)), although with chronic use of pharmacotherapy the patients often become refractory to the continued effect of L-DOPA. There are many suggested mechanisms for the development of the refractory state, but the simplest is that the patients reach a threshold of cell loss, wherein the remaining cells cannot synthesize sufficient dopamine from the precursor.

Parkinson's disease is the first disease of the brain for which therapeutic intracerebral grafting has been used in humans. Several attempts have been made to provide the neurotransmitter dopamine to cells of the diseased basal ganglia of Parkinson's patients by homografting adrenal medullary cells to the brain of affected patients. (Backlund et al., *J. Neurosurc.* 62:169-173 (1985); Madrazo et al., *New Eng. J. Med.* 316:831-836 (1987)). The transplantation of other donor cells such as fetal brain cells from the substantianigra, an area of the brain rich in dopamine-containing cell bodies and also the area of the brain most affected in Parkinson's disease, has been shown to be effective in reversing the behavioral deficits induced by selective dopaminergic neurotoxins. (Bjorklund et al., *Ann. N.Y. Acad. Sci.* 457:53-81 (1986); Dunnett et al., *Trends Neurosci.* 6:266-270 (1983)). These experiments suggest that synaptic connectivity may not be a requisite for a functional graft and that it may be sufficient to have cells constitutively producing and secreting dopamine in the vicinity of the defective cells.

With this background, it seems likely that Parkinson's disease is a candidate disease for the transplantation of genetically engineered cells, because (1) the chemical deficit is well known (dopamine), (2) the human and rat genes for the rate-limiting enzyme in the production of dopamine have been cloned (tyrosine hydroxylase), (3) the anatomical localization of the affected region has been identified (basal ganglia), and (4) synaptic connectivity does not appear to be required for complete functional restoration.

The recent demonstration of genetic components in a rapidly growing list of other CNS diseases, including Huntington's disease, (Gusella et al., *Nature* 306:234-238 (1983)) Alzheimer's disease, (Delabar et al., *Science, N.Y.* 235;1390-1392 (1987); Goldgaber et al., *Science, N.Y.* 235:877-880 (1987); St. George-Hyslop et al., Science, N.Y. 235:885-890 (1987); Tanzi et al., *Science, N.Y.* 235:880-884 (1987); bipolar disease (Baron et al., *Nature* 326:289-292 (1987)); schizophrenia (Sherrington et al., *Nature* 336:164-167 (1988) and many other major human diseases, suggests that these other CNS diseases will eventually become accessible to gene therapy approaches.

In parallel to the progress in neurobiology during the past several decades, advances in an understanding of molecular biology and the development of sophisticated molecular genetic tools have provided new insights into human disease in general. As a result, medical scientists and geneticists have developed a profound understanding of many human diseases at the biochemical and genetic levels. The normal and abnormal biochemical features of many human genetic diseases have become understood, the relevant genes have been isolated and characterized, and early model systems have been developed for the introduction of functional wild-type genes into mutant cells to correct a disease phenotype. (Anderson, *Science* 226:401-409 (1984)). The extension of this approach to whole animals, that is, the correction of a disease phenotype in vivo through the use of the functional gene as a pharmacologic agent, has come to be called "gene therapy". (Friedmann et al., *Science* 175:949-955 (1972); Friedmann, Gene Therapy Fact and Fiction, Cold Spring Harbor Laboratory, N.Y. (1983)). Gene therapy is based on the assumption that the correction of a disease phenotype can be accomplished either by modification of the expression of a resident mutant gene or the introduction of new genetic information into defective or damaged cells or organs in vivo.

At present, techniques for the ideal versions of gene therapy, that is through site-specific gene sequence correction or replacement in vitro, are just beginning to be conceived but are not yet well developed. Therefore, most present models of gene therapy are actually genetic augmentation rather than replacement models and rely on the development of efficient gene-transfer systems to introduce functional, wild-type genetic information into genetically defective cells in vitro and in vivo. To be clinically useful, the availability of efficient delivery vectors for foreign DNA sequences (transgenes) must be combined with easy accessibility of suitable disease-related target cells or organs and with the development of techniques to introduce the vector stably and safely into those target cells.

Model systems for the genetic and phenotypic correction of simple enzymatic deficits are now being developed and studied, as is the identification of the appropriate potential recipient cells and organs associated with specific metabolic and genetic diseases. Evidence has recently been obtained to show that foreign genes introduced into fertilized mouse eggs can correct disease phenotype. (Constantini et al., *Science* 233:1192-1194 (1986); Mason et al., *Science* 234:1372-1378 (1986); and Readhead et al., *Cell* 48:703-712 (1987)).

A great deal of attention has recently been paid to the use of gene delivery vectors derived from murine retroviruses (Anderson, *Science* 226:401-409 (1984); Gilboa et al, *Biotechniques* 4:504-512 (1986)) for gene transfer at later stages of development. Gene transfer in vitro using such retroviral vectors is extremely efficient for a broad range of recipient cells, the vectors have a suitably large capacity for added genes, and infection with them does little metabolic or genetic damage to recipient cells. (Shimotohno et al., *Cell* 26:67-77 (1981); Wei et al., *J. Virol.* 39:935-944 (1981); Tabin et al., *Molec. Cell. Biol.* 2:426-436 (1982)). Several useful systems have demonstrated that the expression of genes introduced into cells by means of retroviral vectors can correct metabolic aberrations in vitro in several human genetic diseases associated with single-gene enzyme deficiencies. (Kantoff et al., *Proc. Nat'l. Acad. Sci. USA* 83:6563-6567 (1986); Willis et al., *J. Biol. Chem.* 259:7842-7849 (1984)). There has been particular interest in bone marrow as a potential target organ for this approach to gene therapy because of the prevalence and importance of disorders of bone marrow-derived cell lineages in a variety of major human diseases, including the thalassemias and sickle-cell anemia, Gaucher's disease, chronic granulomatous disease (CGD) and immunodeficiency disease resulting from deficiencies of the purine pathway enzymes, adenosine deaminase (ADA) and purine nucleoside phosphorylase (PNP) (Kantoff, supra; McIvor et al., *Molec. Cell. Biol.* 7:838-846 (1987); Soriano et al., *Science* 234:1409-1413 (1986); Willis et al., supra)). Other metabolically important target organs, such as the liver, have also recently become theoretically susceptible for genetic manipulation through the demonstration of infection of cells from such organs with viral vectors (Wolff et al., *Proc. Nat'l Acad. Sci. USA* 84:3344-3348 (1987)). Furthermore, the discovery of numerous cell-specific regulatory signals such as cis-acting enhancers, tissue-specific promoters and other sequences may provide tissue specific gene expression in many other organs even after general, non-specific infections and gene transfer in vivo (Khoury et al., *Cell* 33:313-314 (1983); Serflin et al., *Trends Genet.* 1:224-230 (1985)).

A recently developed model of gene therapy uses target cells removed from a subject, placed in culture, genetically modified in vitro, and then re-implanted into the subject (Wolff et al., *Rheumatic Dis. Clin. N. Amer.* 14(2):459-477 (1988); Eglitis et al. *Biotechnicues* 6:608-614 (1988); Ledley, *J. Pediatrics* 110:1-8 (1987)). Target cells have included bone marrow stem cells (Joyner et al., *Nature* 305:556-558 (1983); Miller et al., *Science* 225:630-632 (1984); Williams et al., *Nature* 310:476-480 (1984)); fibroblasts (Selden et al., *Science* 236:714-718 (1982); Garver et al., *Proc. Nat'l Acad. Sci. USA* 84:1050-1054 (1987) and St. Louis et al., *Proc. Nat'l. Acad. Sci. USA* 85:3150-3154 (1988)), keratinocytes (Morgan et al., *Science* 237:1476-1479 (1987)) and hepatocytes (Wolff et al., *Proc. Nat'l. Acad. Sci. USA* 84:3344-3348 (1987)). This indirect approach of in vivo gene transfer is necessitated by the inability to transfer genes efficiently directly into cells in vivo. Although there has been some recent progress towards genetically modifying neurons in culture (Geller et al., *Science* 241:1667-1669 (1988)), this indirect approach of in vivo gene transfer has not yet been applied to the CNS.

There are several ways to introduce a new function into target cells in the CNS in a phenotypically useful way i.e. to treat defects, disease or dysfunction (FIG. 1). The most direct approach, which bypasses the need for cellular grafting entirely, is the introduction of a transgene directly into the cells in which that function is aberrant as a consequence of a developmental or genetic defect, i.e. neuronal cells in the case of Tay-Sachs disease, possibly Lesch-Nyhan disease, and Parkinson's disease (1, in FIG. 1). Alternatively, a new function is expressed in defective target cells by introducing a genetically modified donor cell that could establish tight junction or other contacts with the target cell (2, in FIG. 1). Some such contacts are known to small molecules from one cell to another, leading to phenotypic changes in the recipient cell (Lowenstein, *Biochim. Biochys. Actg.* 560:1-66 (1979)). This process has been called "metabolic co-operation" and is known to occur between fibroblasts and glial cells (Gruber et al., *Proc. Nat'l. Acad. Sci. USA* 82:6662-6666 (1985)), although it has not yet been demonstrated conclusively in neurons. Still other donor cells could express and secrete a diffusible gene product that can be taken up and used by nearby defective target cells (3, in FIG. 1). The donor cells may be genetically modified in vitro or alternatively they may be directly infected in vivo (4, in FIG. 1). This type of "co-operativity" has been demonstrated with CNS cells, as in the case of NGF-mediated protection of cholinergic neuronal death following CNS damage (Hefti, *J. Neurosci.* 6:2155 (1986); Williams et al., *Proc. Nat'l Acad. Sci. USA* 83:9231-9235 (1986)). Finally, an introduced donor cell infected with not only replication-defective vector but also replication-competent helper virus, could produce locally high liters of progeny virus that might in turn infect nearby target cells to provide a functional new transgene (5, in FIG. 1).

There are several types of neurons in the mammalian brain. Cholinergic neurons are found within the mammalian brain and project from the medial septum and vertical limb of the diagonal band of Broca to the hippocampal formation in the basal forebrain. The short, nerve-like portion of the brain connecting the medial septum and vertical limb of the diagonal band with the hippocampal formation is termed the "fimbria fornix". The fimbria fornix contains the axons of the neurons located in the medial septum and diagonal band. An accepted model of neuron survival in vivo is the survival of septal cholinergic neurons after fimbria fornix transection or lesion (also termed "axotomy"). Axotomy severs the cholinergic neurons in the septum and diagonal band and results in the death of up to one-half of the cholinergic neurons (Gage et al., *Neuroscience* 19:241-256 (1986)). This degenerative response is attributed to the loss of trophic support from nerve growth factor (NGF), which is normally transported retrogradely in the intact brain from the hippocampus to the septal cholinergic cell bodies (Korsching et al., *Proc. Nat'l. Acad. Sci. USA* 80:3513 (1983); Whittemore et al., *Proc. Nat'l. Acad. Sci. USA* 83:817 (1986); Shelton et al., *Proc. Nat'l Acad. Sci USA* 83:2714 (1986); Larkfors et al., *J. Neurosci. Res.* 18:525 (1987); and Seilor et al., *Brain Res.* 300:33 (1984)).

Studies have shown that chronic intra-ventricular administration of NGF before axotomy will prevent cholinergic neuron death in the septum (Hefti, *J. Neurosci.* 8:2155-2162 (1986); Williams et al., *Proc. Nat'l Acad. Sci. USA* 83:9231 (1986); Kromer, *Science L* 235 214 (1987); Gage et al., *J. Comp. Neurol.* 269:147 (1988)). Fimbria fornix transection thus provides an in vivo model for determining at various points in time the ability of various therapies to prevent retrograde neuronal death.

It would be advantageous to develop procedures for gene transfer via efficient vectors followed by intracerebral grafting of the genetically modified cells in vivo to treat disorders of the CNS.

SUMMARY OF THE INVENTION

The present invention provides methods for treating defects, disease or damage of cells in the central nervous system by grafting genetically modified donor cells into the central nervous system to produce a molecule that directly or indirectly provides an ameliorative effect on the cells. The cells may be modified using viral or retroviral vectors containing an inserted therapeutic transgene encoding a product which directly or indirectly affects the cells, or by other methods of introducing foreign DNA into a cell. The cells may be cultured and injected in suspension into the central nervous system and may be co-administered with a therapeutic agent for treating disease or damaged cells in the central nervous system. The methods include grafting accompanied by implanting of material to facilitate reconnection or ameliorative interactions of injured neurons.

BRIEF DESCRIPTION OF THE DRAWINGS

FIG. 6a–FIG. 16f are photomicrographs of primary rat fibroblasts previously infected with hypoxanthine quanine phosphoribosyl transferase (HPRT) that have been implanted in rat basal ganglia as described in Example 1, infra. (FIG. 6a, FIG. 6d=anti-fibronectin; FIG. 6b, FIG. 6e=cresyl violet; FIG. 6c, FIG. 6f=GFAP; magnification: FIG. 6a–FIG. 6c=88×; FIG. 6d–FIG. 6f=440×).

FIG. 7 is photographs of isoelectric focusing gels for HPRT enzymatic activity of brain extracts from basal ganglia as described in Example I, infra.

FIG. 8 is a depiction of the circular restriction map of vector pLLRNL as described in Example II, infra.

FIG. 9 is a depiction of the circular restriction map of vector pPR1 as described in Example II, infra.

FIG. 10 is a depiction of the circular restriction map of vector pUCRH as described in Example II, infra.

FIG. 11 is a diagrammatic depiction of the linear restriction map of the integrated NGF retroviral vector PLN.8RNL containing the 777 base pair Hgal-Pstl fragment of mouse nerve growth factor (NGF) cDNA under control of the viral 5' long terminal repeat as described in Example II, infra (arrows indicate transcription initiation sites; LTR=long terminal repeat; psi ($\psi$)=retroviral packaging signal; RSV=Rous sarcoma virus promoter; neo®=neomycin-resistance gene marker.)

FIG. 12 is a depiction of the circular restriction map of vector pLN.8RNL as shown in FIG. 11 and described in Example II, infra.

FIG. 13a–FIG. 13f are photomicrographs of immunohistochemical staining for fibronectin and ChAT as described in Example II, infra (FIG. 13a, FIG. 13b=fibronectin staining in fibroblasts grafted into the fimbria fornix cavity; FIG. 13c–13f=coronal sections taken through the medial septum of tissue stained for ChAT; FIG. 13a, FIG. 13c, FIG. 13e=animal with graft of retrovirus-infected cells; FIG. 13b, FIG. 13d, FIG. 13f=animal with graft of control cells; magnification; FIG. 13a and FIG. 13b=20×FIG. 13c and FIG. 13d=70×; FIG. 13e and FIG. 13f=220×).

FIG. 14 is a graph showing survival of ChAT-immunoreactive cells in the septum of a rat in the presence and absence of NGF as described in Example II, infra.

FIG. 15c=higher power magnification of FIG. 15a through the medial septum; FIG. 15e=high power magnification of FIG. 15a through the dorsal lateral quadrant of the septum; FIG. 15b, FIG. 15d, FIG. 15f=animal grafted with control cells as described for FIG. 15a, FIG. 15c, FIG. 15e; magnification: FIG. 15a, FIG. 15b=20×; FIG. 15c–FIG 15f=220×).

FIG. 16 is a diagrammatic depiction of the linear restriction map of pLTHRNL retroviral integrated vector as described in Example III, infra (arrows indicate the location of the promoters and the direction of transcription; LTR=long terminal repeat; RSV =modified RSV promoter; Neo®=neomycin-resistance gene marker).

FIG. 18a, FIG. 18c=10×; FIG. 18b, FIG. 18d=20×).

DETAILED DESCRIPTION OF THE INVENTION

In order that the invention herein described may be more fully understood, the following detailed description is set forth.

The present invention relates to a process for grafting genetically modified donor cells into the central nervous system (CNS) to treat disease or trauma of the CNS. More particularly, the invention relates to the use of vectors carrying foreign gene inserts (transgenes) to modify donor cells to produce a molecule that is capable of directly or indirectly affecting cells in the CNS to repair damage sustained by the cells from defects, disease or trauma. Preferably, for treating defects, disease or damage of cells in the CNS, donor cells such as fibroblasts are modified by introduction of a retroviral vector containing a transgene, for example a gene encoding nerve growth factor (NGF) protein. The genetically modified fibroblasts are grafted into the central nervous system, for example the brain, to treat defects, disease such as Alzheimer's or Parkinson's, or injury from physical trauma, by restoration or recovery of function in the injured neurons as a result of production of the expressed transgene product from the genetically modified donor cells.

GENE TRANSFER INTO DONOR CELLS IN VITRO

Figure 1:
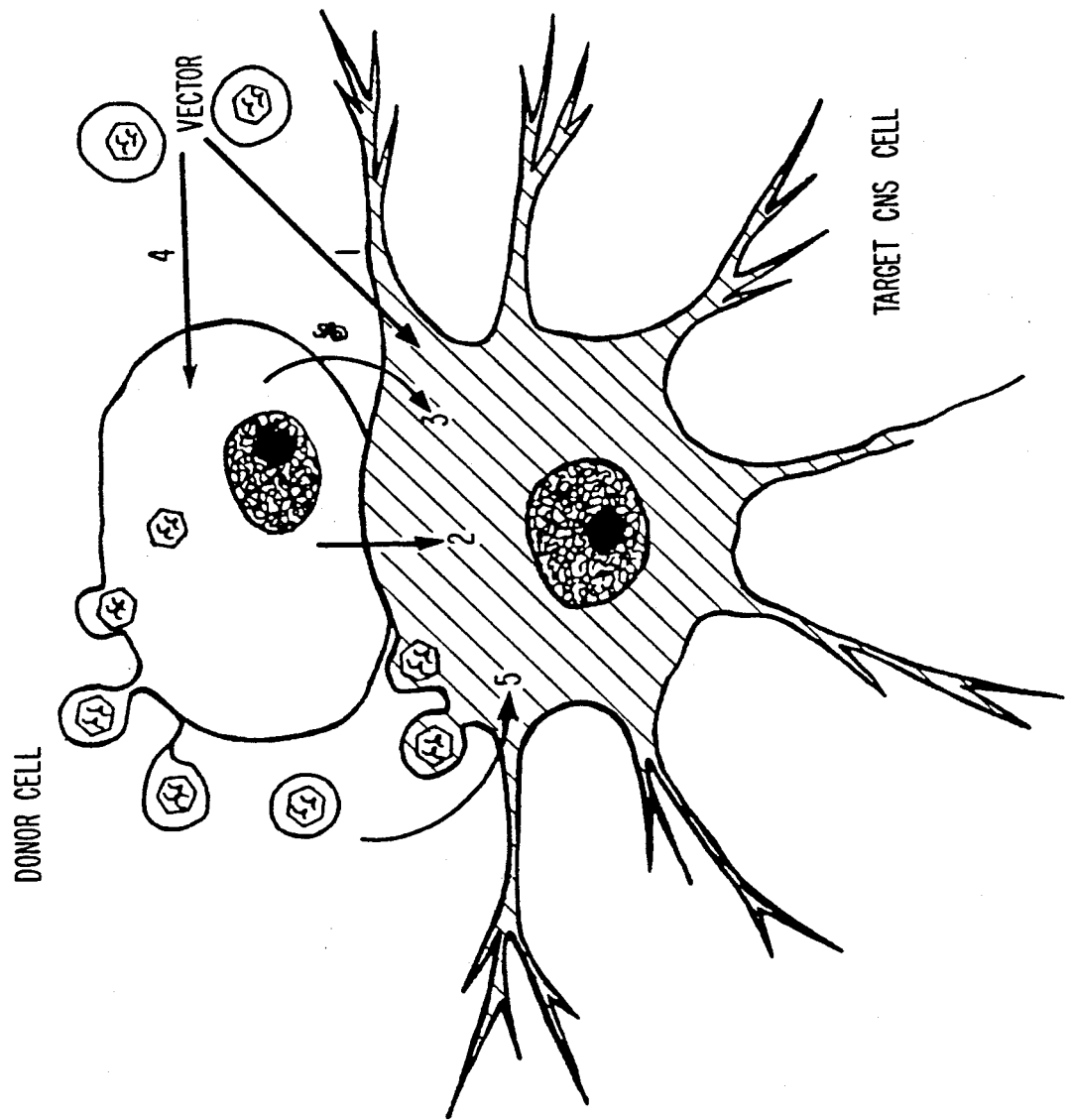
FIG. 1 is a diagrammatic representation of methods for introducing and analyzing the effect of a new function into target cells.
Figure 2:
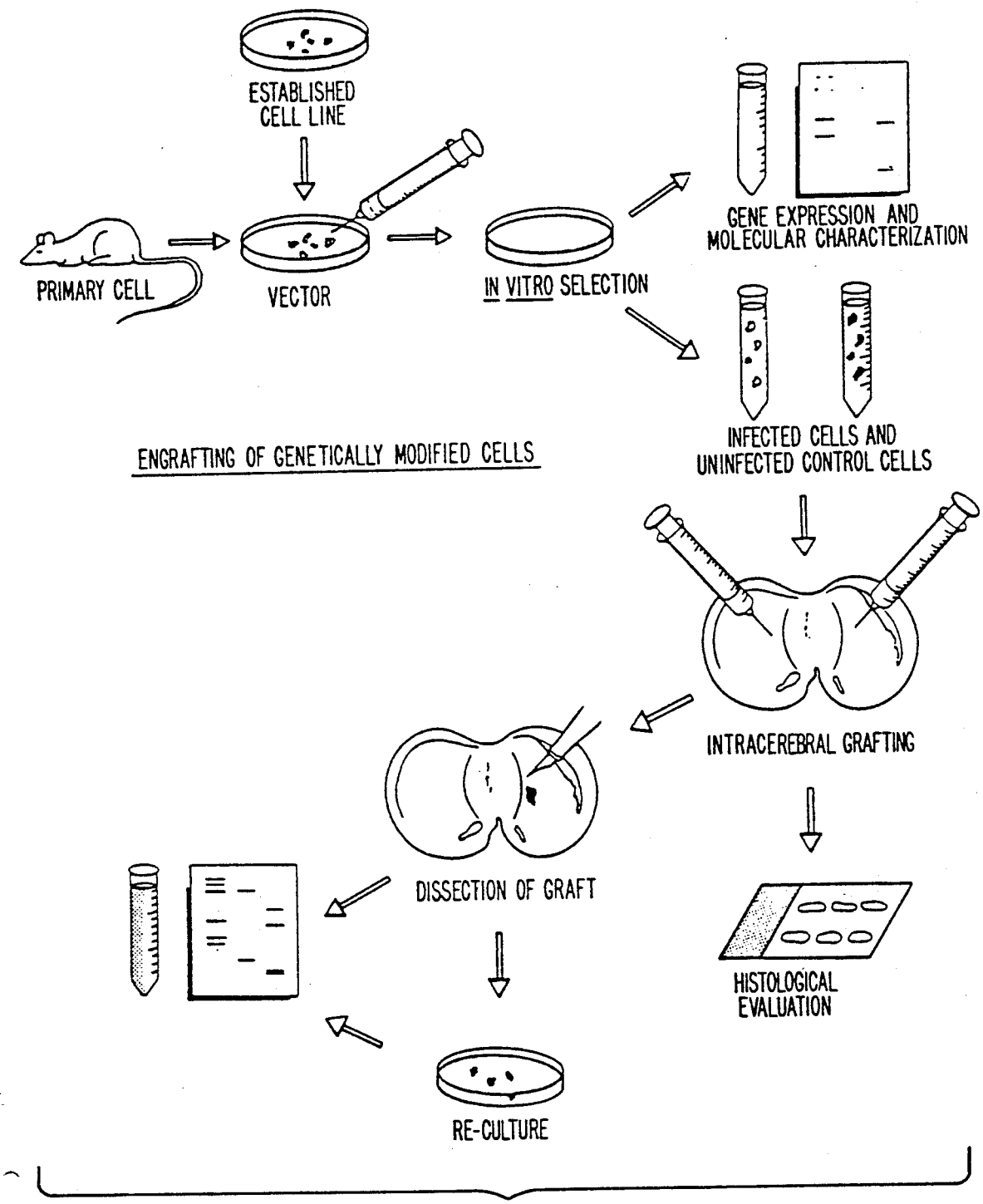
FIG. 2 is a diagrammatic representation of strategies for introducing a new function into target cells in the CNS using genetically modified donor cells.

The strategy for transferring genes into donor cells in vitro is outlined in FIG. 2 and includes the following basic steps: (1) selection of appropriate model "reporter" genes or transgenes whose expression is correlated with CNS disease or dysfunction; (2) selection and development of suitable and efficient vectors for gene transfer; (3) preparation of donor cells from primary cultures or from established cell lines; (4) demonstration that the donor implanted cells expressing the new function are viable and can express the transgene product stably and efficiently; (5) demonstration that the transplantation causes no serious deleterious effects; and (6) demonstration of a desired phenotypic effect in the host animal.

GENETIC MODIFICATION OF DONOR CELLS

The methods described below to modify donor cells using retroviral vectors and grafting into the CNS are merely for purposes of illustration and are typical of those that might be used. However, other procedures may also be employed, as is understood in the art.

Most of the techniques used to transform cells, construct vectors and the like are widely practiced in the art, and most practitioners are familiar with the standard resource materials which describe specific conditions and procedures. However, for convenience, the following paragraphs may serve as a guideline.

CHOICE OF VECTOR

Although other vectors may be used, preferred vectors for use in the methods of the present invention are viral (including retroviral) vectors. The viral vector selected should meet the following criteria: 1) the vector must be able to infect the donor cells and thus viral vectors having an appropriate host range must be selected; 2) the transferred gene should be capable of persisting and being expressed in a cell for an extended period of time without causing cell death for stable maintenance and expression in the cell; and 3) the vector should do little, if any, damage to target cells. Murine retroviral vectors offer an efficient, useful, and presently the best-characterized means of introducing and expressing foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

GENERAL METHODS FOR VECTOR CONSTRUCTION

Construction of suitable vectors containing the desired therapeutic gene coding and control sequences employs standard ligation and restriction techniques which are well understood in the art (see Maniatis et al., in *Molecular Cloninc: A Laboratory Manual*, Cold Spring Harbor Laboratory, N.Y. (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1 µg of plasmid or DNA sequences is cleaved by one unit of enzyme in about 20 µl of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499-560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM MgCl$_2$, 6 mM DTT and 5-10 µM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15-50 µl volumes under the following standard conditions and temperatures: 20 mM Tris-Cl pH 7.5, 10 mM MgCl$_2$, 10 mM DTT, 33 mg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C (for "blunt end" ligation). Intermolecular "sticky end" ligations are usually performed at 33-100 µg/ml total DNA concentrations (5-100 nM total end concentration). Intermolecular blunt end ligations (usually employing a 10-30 fold molar excess of linkers) are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na+ and Mg+2 using about 1 unit of BAP or CIP per mg of vector at 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site-specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Methods of preparation of retroviral vectors have been described (Yee et al., *Cold Spring Harbor Symp. on Quant. Biol.* Vol. LI, pp 1021-1026 (1986); Wolff et al., *Proc. Nat'l Acad.* 4:3344-3348 (1987); Jolly et al., *Meth. in Enzymol.* 149:10-25 (1987); Miller et al., *Mol. Cell. Biol.* 5:431-437 (1985); and Miller, et al., *Mol. Cell. Biol.* 6:2895-2902 (1986) and Eglitis et al., *Biotechniques* 6:608-614 (1988)) and are now in common use in many laboratories. Retroviral vectors contain retroviral long terminal repeats (LTRs) and packaging (psi) sequences, as well as plasmid sequences for replication in bacteria and may include other sequences such as the SV40 early promoter and enhancer for potential replication in eukaryotic cells. Much of the rest of the viral genome is removed and replaced with other promoters and genes. Vectors are packaged as RNA in virus particles following transfection of DNA constructs into packaging cell lines. These include psi (Ψ)2 which produce viral particles that can infect rodent cells and ψAM and PA 12 which produce particles that can infect a broad range of species.

Figure 3:
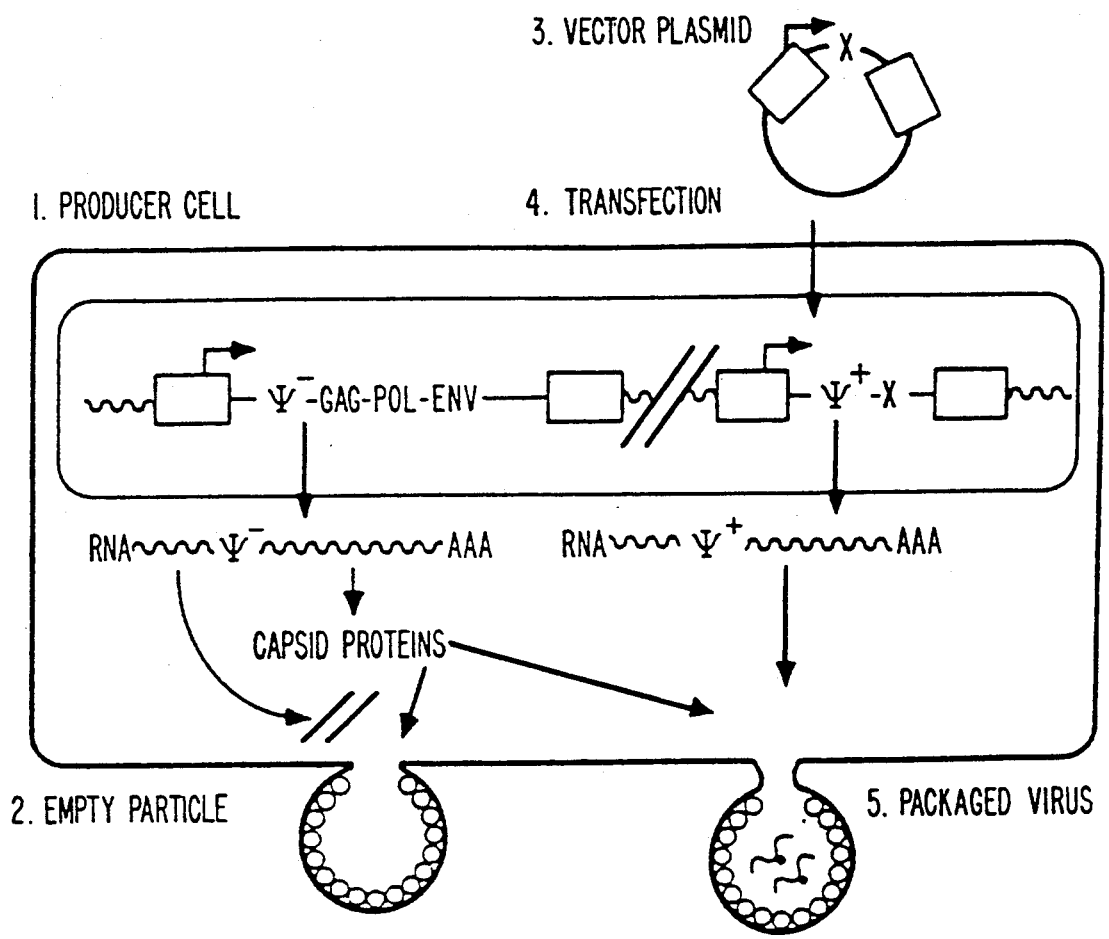
FIG. 3 is a diagrammatic depiction of the preparation of transmirable retrovirus vectors containing a transgene. (GAG=group specific antigen; Env=envelope; POL=reverse transcriptase).

In a preferred viral vector the transgene is brought under the control of either the viral LTR promoter-enhancer signals or of an internal promoter, and retained signals within the retroviral LTR can still bring about efficient integration of the vector into the host cell genome. To prepare transmissible virus (FIG. 3), recombinant DNA molecules of such defective vectors are transfected into "producer" cell lines that contain a provirus expressing all of the retroviral functions required for packaging of viral transcripts into transmissible virus particles, but lacking the crucial packaging signal $\Psi$ for encapsidation of RNA transcripts of the provirus into mature virus particles. These include the group specific antigen (GAG) and envelope (ENV) genes which encode capsid proteins and reverse transcriptase (POL). Because of this deletion, transcripts from the helper cannot be packaged into viral particles and the producer cells, therefore, generate only empty virus particles. However, an integrated defective retroviral vector introduced into the same cell by means of calcium-phosphate-mediated transfection (Graham and Vander Eb, *Virol.* 52:456-467 (1973)) in which the GAG, ENV and POL genes have been replaced by the transgene (X) with the intact psi sequence, produces transcripts that can be packaged in trans since they do contain the packaging sequence. The cells contain 2 provirus sequences integrated into different sites of the host cell genome. Because RNA transcripts from the newly introduced provirus contain the packaging sequence they are efficiently encapsidated into virus particles by means of viral functions produced in trans. Ideally, the result is the production by the cells of infectious particles carrying the transgene free of replication-competent wild-type helper virus. In most, but not necessarily all models of gene therapy, the production of helper virus is probably undesirable since it may lead to spreading infection and possibly proliferative disease in lymphoid or other tissue in the host animal.

Since herpes viruses are capable of establishing a latent infection and an apparently non-pathogenic relationship with some neural cells, herpes based vectors, e.g. HSV-1, may be used. Similarly, it should be possible to take advantage of an eventual improved understanding of other human and animal viruses that infect cells of the CNS efficiently, such as rabies virus, measles, and other paramyxoviruses and the human immunodeficiency retrovirus (HIV), to develop useful delivery and expression vectors. In most cases, with the exception of rabies virus, these viruses are not truly neurotropic for infection, but rather have a much more general susceptible host cell range. They seem, rather, to appear to be neurotropic because the metabolic and physiological effects of infection are most pronounced in cells of the CNS. It is, therefore, likely that many vectors derived from these viruses will be similarly promiscuous in their cell range, and that CNS specificity for expression must be conferred by the use of appropriate cell-specific enhancer, promoter and other sequences, such as those that regulate the oligodendroglial-specific expression of JC virus, glial-specific expression of the proteolipid protein and glial fibrillary acidic protein (GFAP) genes, and other possible CNS specific functions in the mouse.

Other virus vectors that may be used for gene transfer into cells for correction of CNS disorders include retroviruses such as Maloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia; rabies and poliovirus and other human and animal viruses.

A possible problem posed by the use of defective viral vectors is the potential for the eventual emergence or "rescue" of pathogenic, replication-competent, wild-type virus by recombination with endogenous virus-like or other cellular sequences. This possibility can be reduced through the elimination of all viral regulatory sequences not needed for the infection, stabilization or expression of the vector.

In addition to the above-described methods for inserting foreign DNA transgenes into donor cells other methods may be used. For example, non-vector methods include nonviral physical transfection of DNA into cells; for example, microinjection; electroporation (Toneguzzo et al., *Molec. Cell. Biol.* 6:703-706 (1986)); chemically mediated transfection such as calcium phosphate transfection (Graham et al., *Virol.* 52:456-467 (1973)); liposomal mediated transfection and other methods known in the art.

CHOICE OF DONOR CELLS

The choice of donor cells for implantation depends heavily on the nature of the expressed gene, characteristics of the vector and the desired phenotypic result. Because retroviral vectors are thought to require cell division and DNA synthesis for efficient infection, integration and gene expression (Weiss et al., *RNA Tumor viruses.* 2nd Ed., Weiss et al., eds., Cold Spring Harbor Press, N.Y. (1985)), if such vectors are used the donor cells are preferably actively growing cells such as primary fibroblast culture or established cell lines, replicating embryonic neuronal cells or replicating adult neuronal cells in selected areas such as the olfactory mucosa and possibly developing or reactive glia. Other suitable donor cells include fibroblasts, neurons, glial cells, keratinocytes, hepatocytes, connective tissue cells, ependymal cells, chromaffin cells and other mammalian cells susceptible to genetic manipulation and grafting using the methods of the present invention. The application of methods to induce a state of susceptibility in stationary, non-replicating target cells may make many other cell types suitable targets for viral transduction. For instance, methods have been developed that permit the successful retroviral vector infection of primary cultures of adult rat hepatocytes, ordinarily refractory to infection with such vectors, and similar methods may be helpful for a number of other cells (Wolff et al., *Proc. Nat'l Acad. Sci. USA* 84:3344-3348 (1987)). In addition, the development of many other kinds of vectors derived from herpes, vaccinia, or other viruses, as well as the use of efficient, non-viral methods for introducing DNA into donor cells such as the recently developed electroporation technique, (Toneguzzo et al., *Molec. Cell. Biol.* 6:703-706 (1986)) may be used for gene transfer into many other cells presently not susceptible to retroviral vector infection.

MECHANISMS OF PHENOTYPIC CORRECTION BY DONOR CELLS

Grafting

The methods of the invention contemplate intracerebral grafting of donor cells containing a transgene insert to the region of the CNS having sustained, defect, disease or trauma.

Neural transplantation or "grafting" involves transplantation of cells into the central nervous system or into the ventricular cavities or subdurally onto the surface of a host brain. Conditions for successful transplantation include: 1) viability of the implant; 2) retention of the graft at the site of transplanation; and 3) minimum amount of pathological reaction at the site of transplantation.

Methods for transplanting various nerve tissues, for example embryonic brain tissue, into host brains have been described in *Neural Grafting in the Mammalian CNS*, Bjorklund and Stenevi, eds., (1985) Das, Ch. 3 pp. 23-30; Freed, Ch. 4, pp. 31-40; Stenevi et al., Ch. 5, pp. 41-50; Brundin et al., Ch. 6, pp. 51-60; David et L al., Ch. 7, pp. 61-70; Seiger, Ch. 8, pp. 71-77 (1985), incorporated by reference herein. These procedures include intraparenchymal transplantation, i.e. within the host brain (as compared to outside the brain or extraparenchymal transplantation) achieved by injection or deposition of tissue within the host brain so as to be apposed to the brain parenchyma at the time of transplantation (Das, sucra).

The two main procedures for intraparenchymal transplantation are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 30% collagen to form a plug of solid tissue which may then be implanted into the ventricle to prevent dislocation of the graft. For subdural grafting, the cells may be injected around the surface of the brain after making a slit in the dura.

Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The cell suspension is drawn up into the syringe and administered to anesthetized graft recipients. Multiple injections may be made using this procedure. The age of the donor tissue, i.e. the developmental stage may affect the success of cell survival after grafting.

The cellular suspension procedure thus permits grafting of genetically modified donor cells to any predetermined site in the brain or spinal cord, is relatively non-traumatic, allows multiple grafting simultaneously in several different sites using the same cell suspension, and permits mixtures of cells from different anatomical regions.

For transplantation into cavities, which may be preferred for spinal cord grafting, tissue is removed from regions close to the external surface of the CNS to form a transplantation cavity, for example as described by Stenevi et al., supra, by removing bone overlying the brain and stopping bleeding with a material such a gelfoam. Suction may be used to create the cavity. The graft is then placed in the cavity. More than one transplant may be placed in the same cavity using injection of cells or solid tissue implants.

Grafting of donor cells into a traumatized brain, will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

PREPARATION OF DONOR CELLS

The donor cells must be property prepared for grafting. For example, for injection of genetically modified donor cells according to the present invention, cells such as fibroblasts obtained from skin samples are placed in a suitable culture medium for growth and maintenance of the cells, for example a solution containing fetal calf serum and allowed to grow to confluency. The cells are loosened from the culture substrate for example using a buffered solution such as phosphate buffered saline (PBS) containing 0.05% trypsin and placed in a buffered solution such as PBS supplemented with 1 mg/ml of glucose; 0.1 mg/ml of $MgCl_2$; 0.1 mg/ml $CaCl_2$ (complete PBS) plus 5% serum to inactivate trypsin. The cells may be washed with PBS using centrifugation and are then resuspended in the complete PBS without trypsin and at a selected density for injection. In addition to PBS, any osmotically balanced solution which is physiologically compatible with the host subject may be used to suspend and inject the donor cells into the host.

In addition, the host must be appropriately prepared for grafting of donor cells. This depends on the site of the host brain for grafting.

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the foreign gene product. The mammalian brain has traditionally been considered to be an immunologically privileged organ, but recent work has shown conclusively that immune responses can be demonstrated to foreign antigens in the rat brain. It is imperative to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life.

The most effective mode and timing of grafting of the transgene donor cells of the invention to treat defects, disease or trauma in the CNS of a patient will depend on the severity of the defect and on the security and course of disease or injury to cells such as neurons in the CNS, the patient's health and response to treatment and the judgment of the treating health professional.

Of course, as in all other gene-transfer systems, the important issues of appropriate or faithful gene expression must be resolved to ensure that the level of gene expression is sufficient to achieve the desired phenotypic effect and not so high as to be toxic to the cell.

The genetic correction of some, or many, CNS disorders may require the establishment or re-establishment of faithful intercellular synaptic connections. Model systems to study these possibilities have not yet been developed and exploited because of the paucity of replicating non-transformed cell-culture systems and the refractoriness of non-replicating neuronal cells to viral infection. However, recent studies, including those involving the immortalization of embryonic hippocampal neuronal cells, suggest that replicating neuronal cell culture systems may soon become available for in vitro gene transfer and then for in vivo implantation. (Geller et al., *Science* 241:1667-1669 (1988)). Such neurons might be susceptible to efficient transduction by retroviral or other viral vectors, and if they are also able to retain other neuronal characteristics, they may be able to establish synaptic connections with other cells after grafting into the brain. Alternatively, there are cells within the CNS that are late to develop, such as the ventral leaf of the dentate gyrus of the hippocampus, or continue to divide through adulthood, such as those in the olfactory mucosa and in the dentate gyrus. Such cells may be suitable targets for retroviral infection.

The use of non-neuronal cells for grafting may preclude the development of specific neural connections to resident target cells of the host. Therefore, the phenotypic effects of fibroblast or other non-neuronal donor cells or target cells in vivo would be through the diffusion of a required gene product or metabolite, through tight junctions ("metabolic co-operation") or through uptake by target cells of secreted donor cell gene products or metabolites. The donor cell may also act as a toxin "sink" by expressing a new gene product and metabolizing and clearing a neurotoxin.

Alternatively, "neural bridges" may be provided which facilitate reconnection between neurons in damaged CNA tissues. Neural bridges have been described (see Aguayo, in *Synaptic Plasticity*, Cotman, ed., N.Y., Gilford press, pp. 457-484 (1985) and Aguayo et al., *Annals of the N.Y. Acad. of Sciences*, 495:1-9 (1987)). Peripheral nerve segments have been used to successfully join the medulla oblongata and upper thoracic spinal cord of an injured rat (David and Aguayo, *Science* 214:931-933 (1981)). Connectivity between the septum and hipposcampus of the brain has also been demonstrated using implants of peripheral homogenates of neurons (Wendt, *Brain Res. Bull.* 15:13-18 (1985)). Thus, the grafted donor cells may serve as neural bridges to facilitate axonal regeneration and reconnection of injured neurons, or may be used in conjunction with neural bridges formed from synthetic or biological materials, for example homogenates of neurons or placenta.

The present invention therefore provides methods for genetically modifying donor cells for grafting CNS to treat defects, disease and injury of the CNS.

The methods of the invention are exemplified by preferred embodiments in which donor cells containing vectors carrying a therapeutic transgene are grafted intracerebrally into a subject to treat disease or trauma. In a first preferred embodiment, the established HPRT-deficient rat fibroblast line 208F, primary rat fibroblasts, and postnatal, day-1 primary rat astrocytes were used to demonstrate that cultured cells genetically modified using retroviral vectors can survive when implanted in the mammalian brain and can continue to express foreign gene products.

In a second preferred embodiment fibroblasts were genetically modified to secrete NGF by infection with a retroviral vector, and the modified fibroblasts were then implanted into the brains of rats with surgical lesions of the fimbria fornix region. The grafted cells survived and produced sufficient NGF to prevent the degeneration of cholinergic neurons that would die without treatment. In addition, the protected cholinergic cells sprouted axons that projected in the direction of the cellular source of NGF.

In a third preferred embodiment fibroblasts were genetically modified to express and secrete L-DOPA by infection with a retroviral vector, and the modified fibroblasts were grafted into the caudate of rats modeling Parkinson's disease as a result of unilateral dopamine depletion. The cells survived and produced sufficient L-DOPA to decrease the rotational movement caused by dopamine depletion.

The methods of the invention also contemplate the use of grafting of transgenic donor cells in combination with other therapeutic procedures to treat disease or trauma in the CNS. Thus, genetically modified donor cells of the invention may be co-grafted with other cells, both genetically modified and non-genetically modified cells which exert beneficial effects on cells in the CNS, such as chromaffin cells from the adrenal gland, fetal brain tissue cells and placental cells. The genetically modified donor cells may thus serve to support the survival and function of the co-grafted, non-genetically modified cells, for example fibroblasts modified to produce nerve growth factor (NGF) in vivo as described in the Examples, infra.

Moreover, the genetically modified donor cells of the invention may be co-administered with therapeutic agents useful in treating defects, trauma or diseases of the CNS, such as growth factors, e.g. nerve growth factor; gangliosides; antibiotics, neurotransmitters, neurohormones, toxins, neurite promoting molecules; and antimetabolites and precursors of these molecules such as the precursor of dopamine, L-DOPA.

In order that the invention described herein may be more fully understood, the following examples are set forth. It should be understood that these examples are for illustrative purposes only and are not to be construed as limiting the scope of this invention in any manner.

EXAMPLE I

Figure 4:
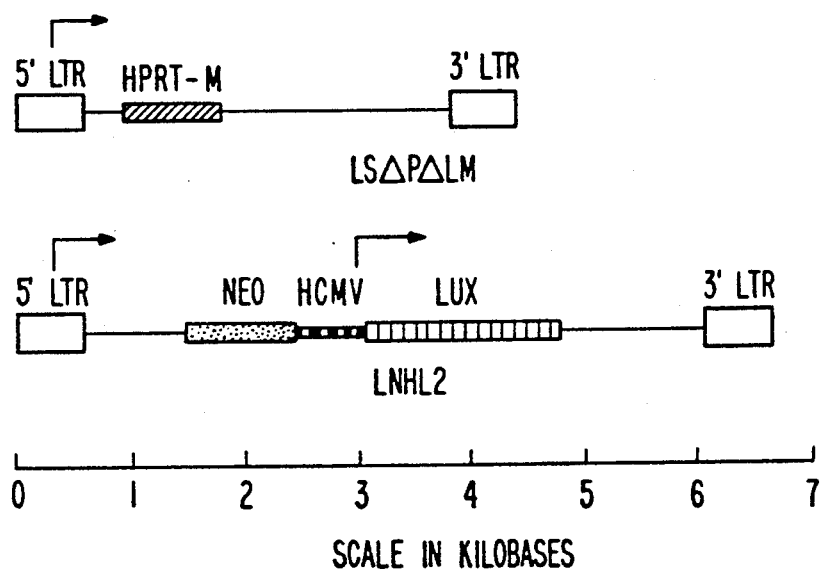
FIG. 4 is a diagrammatic representation of the linear restriction maps of the integrated vectors LSΔPΔLM and pLNHL$_2$ as described in Example I, infra (arrows indicate the location of the promoter and the direction of transcription. The diagonally hatched box of ISΔPΔLM represents the human HPRT cDNA encoding a protein with a novel terminal hexapeptide added by in vitro mutagenesis, LTR=long terminal repeat).

Intracerebral Grafting Of Genetically Modified Cells Expressing HPRT Transgene To The Brain Infection of Cells Donor hypoxanthine guanine phosphoribosyl transferase (HPRT)-deficient 208F rat fibroblast cells (Jolly et al., *Proc. Nat'l Acad. Sci, USA* 80:477-481 (1983)) were infected with the prototype HPRT vector pLSΔPΔLM expressing HPRT cDNA (Miller et al., *Science* 225:630-632 (1984); Yee et al., *Gene* 53:97-104 (1987)) cDNA or with the neo ®-luciferase vector pLNHL2 (Eglitis et al., *Science* 230:1395-1398 (1985); Wolff et al., *Proc. Nat'l Acad. Sci. (USA)* expressing both the Tn5 transposon neomycin-resistance gene (neo ®) and the firefly i luciferase cDNA (de Wet et al., *Molec. Cell. Biol* 7:725-737 (1987)) (FIG. 4). The pLSΔPΔLM vector was derived from vector pLPL2 (Miller et al., *Molec. and Cell Biol.* 6:2895-2902 (1986)) and contains human HPRT cDNA encoding a protein with a novel C-terminal hexapeptide added by in vitro mutagenesis of the translational termination codon (Yee et al., *Gene* 53:97-104 (1987)). Vector pLSΔPΔLM was constructed as follows: Vector pLpLM (Yee et al., *Gene* 53:97-104 (1987)) was digested with XhoI and BamHI to yield a 1.3 Kb fragment which was then ligated into plasmid pLpL2 (Miller, supra) which had also been restricted using XhoI and BamHI. The resulting vector was pLSΔPΔLM.

Figure 5:
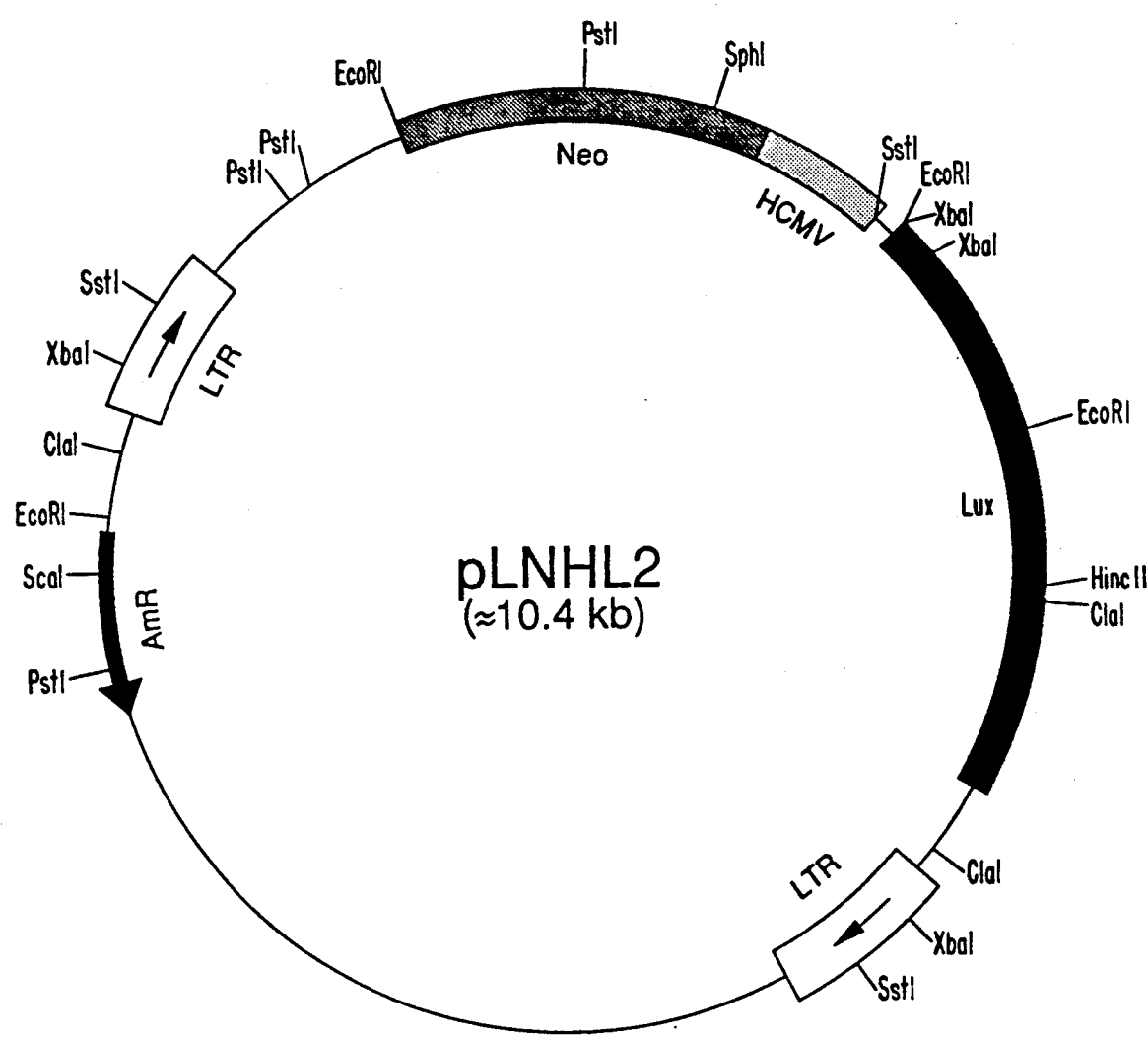
FIG. 5 is a depiction of the circular restriction map of vector pLNHL2 as described in Example I, infra.

The vector pLNHL2 contained the cDNA encoding the firefly luciferase (LUX) and the Tn5 neomycin-resistance gene (neo ®) and the promoter and enhancer of the human cytomegalovirus immediate early gene (HCMV). The 5' and 3' LTRs were derived from cloned murine leukemia virus (MLV) as described by Mason et al., in *Science* 34:1372-1378 (1986)). Vector pLNHL2 was constructed as follows: Plasmid pLNHPL2 (also known as PNHP-1, Yee et al., *Proc. Nat'l Acad. Sci. USA* 84:5197-5209 (1987)) was restricted with BamHI to remove the HPRT DNA sequence. The ends were repaired using Klenow polymerase. Plasmid pSV2A (deWet et al., *Molec. and Cell Biol.*, supra, and supplied by) (Dr. Subramani, University of California, San Diego, Calif.) was restricted with HindIII and SspI to isolate the luciferase fragment. The ends were repaired as above. The BamHI restricted pLNHL2 and HindIII-SspI restricted pSV2A were ligated together forming vector pLNHL2 (FIG. 5).

The cells were grown in selective medium containing hypoxanthine, aminopterin and thymidine (HAT) for cells expressing HPRT and with the neomycin analog G418 for co cells expressing neo ®, respectively, to ensure that only infected cells were used.

Primary fibroblasts and astrocytes were infected with the neo ®-luciferase vector only. HAT-resistant and G418-resistant cells were harvested following incubation overnight with serum-free medium or medium containing rat serum, to reduce the likelihood of immunological response in the rat brain.

Grafting

The cells were resuspended in a balanced glucosesaline solution and injected stereotaxically into several regions of the rat brain using a sterile microsyringe. Between 10,000 and 100,000 cells per microliter were injected at a rate of 1 $\mu$l/min for a total volume of 3-5 $\mu$l. After 1 week to 3 months the animals were killed and areas containing the implanted cells were identified, excised, and examined histologically and biochemically.

Histological Analyses

To evaluate the grafted cells histologically, the rats were perfused transcardially and their brains were sectioned and stained with Nissl stain and cresyl violet for general morphological characterization and with immunocytochemical methods to establish the presence of the specific cell antigenic markers fibronectin for the fibroblasts and glial fibrillary acidic protein (GFAP) for glial cells. Briefly, the sections were rinsed in Tris-buffered-saline (TBS) solution (pH 7.4) containing 0.25% Trtion-X. The sections were incubated for 24 hrs at 4° C. with rabbit polyclonal antibodies to fibronectin (1:2000 dilution) Baralle, University of Oxford, England) and GFAP (Gage et al., *Exp. Neurol.* 102:2-13 (19889); available from Dakopatts, Glostryp, Denmark) diluted 1:1000 in TBS containing 0.25% Trtion-X and 3% goat serum or with the monoclonal antibody, mouse IgG2a, against a membrane polypeptide of rat macrophages, granulocytes and dendritic cells (MRC OX-42, Serotec) diluted 1:100 in TBS containing 0.25% Trtion-X and 1% horse serum. After thorough rinsing, the sections were incubated for 1 hr with biotinylated goat anti-rabbit IgG (Vectastain) diluted 1:200 in 0.1 M TBS containing 0.25% Trtion-X and 15 horse serum, followed by several rinses in TBS containing 0.25% Trtion-X and 1% goat serum or 1% horse serum. The sections were then incubated for 1 hr at room temperature with a complex of avidin and biotinylated horseradish peroxidase (Vectastain, ABC kit, Vector Labs, Burlingame, Calif.) diluted 1:100 in 0.1 M TBS containing 0.25% Trtion-X and 1% goat serum or 1% horse serum, followed by thorough rinses. The peroxidase was visualized by reacting with 0.05%, 3,3-diaminobenzidine tetrahydrochloride (DAB)(Sigma Chemical Co., St. Louis, MO) and 0.05% NiCl2 and 0.01% H2O2 in TBS for 15 min at room temperature.

Figures 6A, 6B, 6C:
Figures 6D, 6E, 6F:
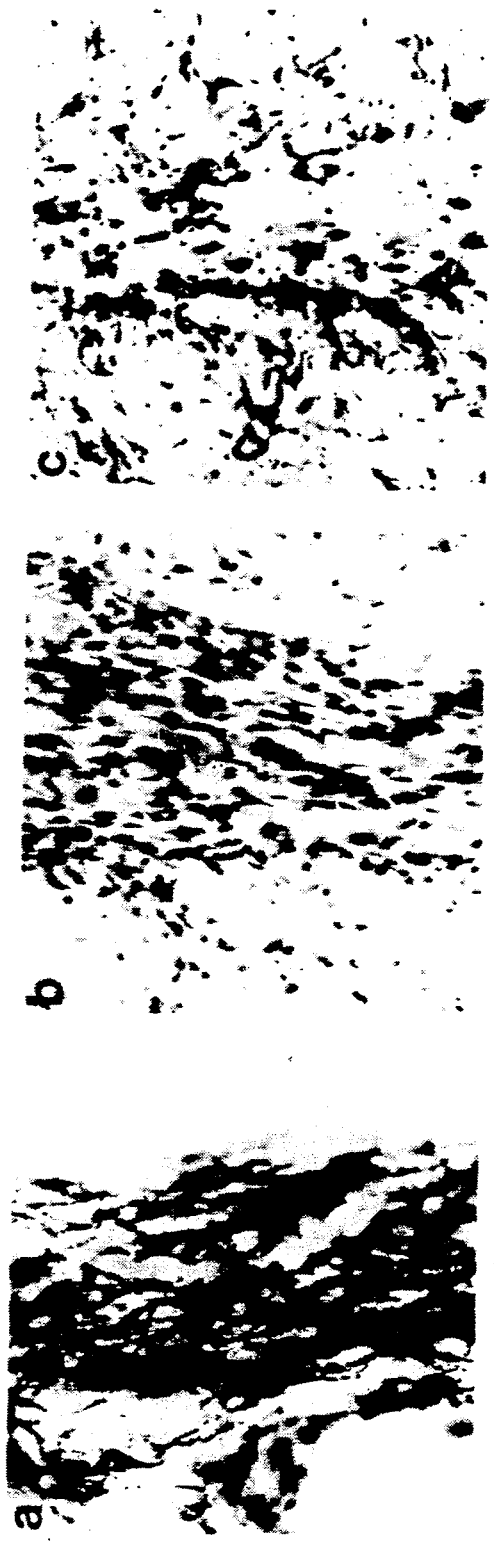

Primary rat fibroblasts grafted to the neostriatum of the rat seven weeks earlier are illustrated in FIG. 6. Serial 40 mm-thick sections were stained with anti-fibronectin (a), cresyl violet (Disbrey et al., *Histological Laboratory Methods*, E. & S. Livingstone, Edinburgh and London (1970)), (b) and anti-GFAP (c). The surviving cells appeared to be intact and to have clumped or aggregated around the area of the injection. The cells displayed an intense staining for fibronectin at the core of the graft, with a clear GFAP-staining derived from reactive gliosis at the edges of the grafts, similar to what one sees with the cannula tract alone. However, little GFAP-staining was observed in the graft itself. With cresyl violet, small, round, darkly stained cells were observed in the region of the graft which could either be microglia or lymphocytes that had infiltrated the area in response to injury. Macrophages could also be detected in many of the grafts. Many of the fibroblasts could be identified by cresyl violet staining by their long thin shape and by the pink pleated sheets of collagenous material surrounding them. The appearance of 208F fibroblasts was similar to the primary fibroblasts (not shown). Astrocyte grafts also had a similar appearance, except they were not fibronectin-positive, and stained for GFAP through the center of the grafts. For all three cell types, no differences were observed between retrovirus-infected cells and control cells. An important feature of these cell suspension grafts is that most of the cells remained aggregated near the site of injection and did not appear, under these circumstances, to migrate very far from the injection site into the host brain. This apparent lack of migration could certainly be different for other donor cell types and graft sites, and therefore the area of the brain into which the cells are to be implanted, the nature of the donor cells, and the phenotype of the target cells for the transgene may be important factors for the selection of donor cells.

Characterization of Implanted Cell

Figure 7:
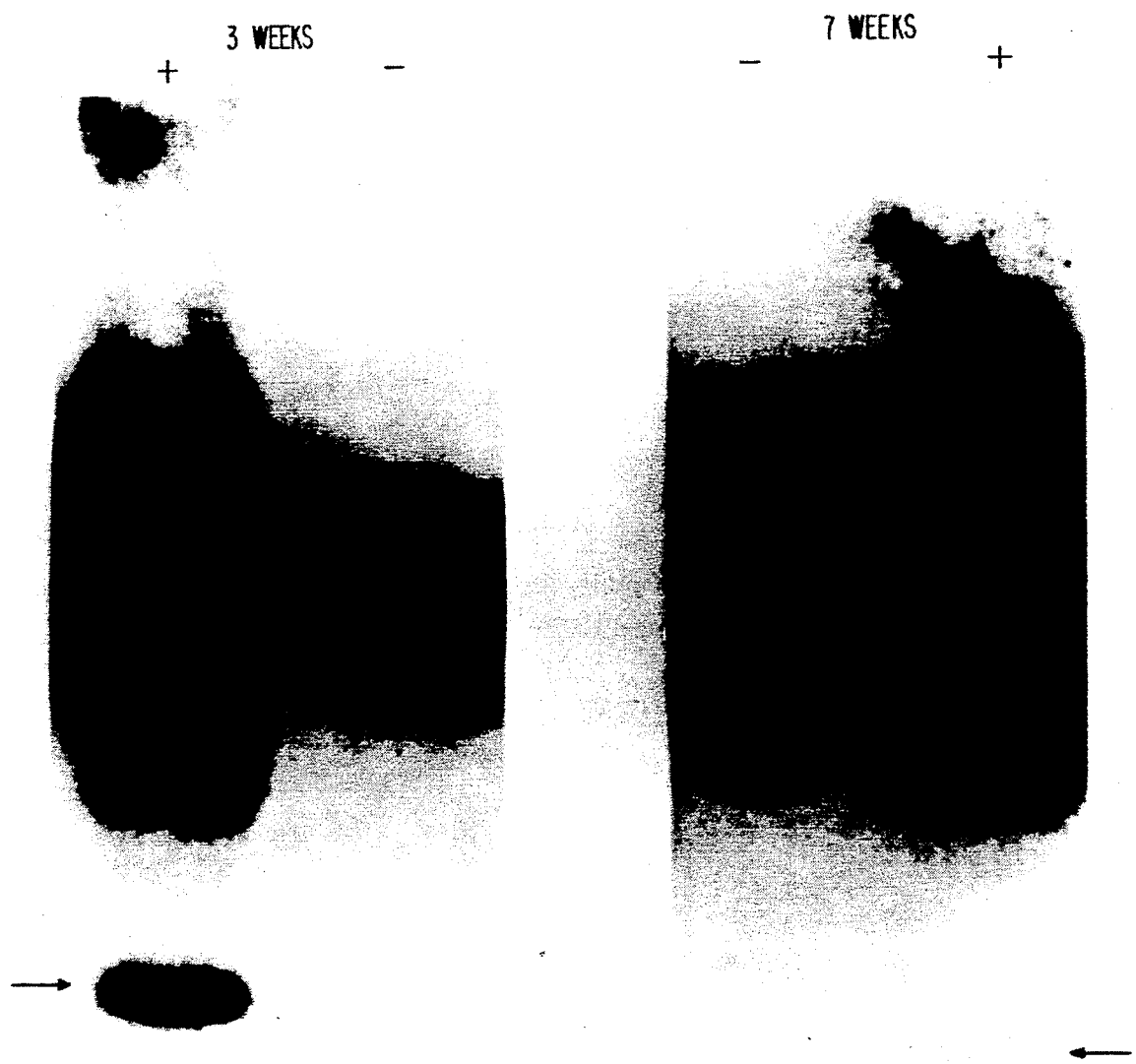

Implanted cells were dissected out and prepared for reculturing and for biochemical and molecular characterization by dissociating the cells with trypsin. For the detection of the human HPRT activity, cell extracts were prepared from the bulk of each sample as previously described and examined by a polyacrylamide gel isoelectric focusing HPRT assay (Jolly et al., *Proc. Nat'l. Acad. Sci. USA)* 80:477-481 (1983); Miller et al., *Proc. Nat'l. Acad. Sci (USA)* 80:4709-4713 (1983); Willis et al., *J. Biol. Chem.* 259:7842-7849 (1984); Miller et al., *Science* 225:630-632 (1984); Gruber et al., *Science* 230:1057-1061 (1985), and Yee et al., *Gene* 53:97-104 (1987)). The remainder of each sample was placed into culture. The results of an HPRT gel assay of rat 208F cells HAT resistance after infection with the HPRT vector implanted into one side of the rat basal ganglia 3 and 7 weeks after transplantation and prior to analysis are shown in FIG. 7.

The presence of human HPRT enzyme activity demonstrates that the infected, genetically modified rat 208F cells grafted into the brain survived and continued to express the HPRT transgene at easily detectable levels for at least 7 weeks. Furthermore, the implanted cells could be successfully recultured, producing cells morphologically identical to the starting cultures. Infection of these cells with helper virus resulted in the production of HPRT virus, confirming the identity of the cells and indicating that the provirus remained intact. Studies with the neo ®-luciferase vector confirm the survival and expression of luciferase-infected cells.

EXAMPLE II

Grafting of Genetically Modified Cells Expressing NGF to the Damaged Brain

The above example demonstrated that cultured cells genetically modified using retroviral vectors can survive when implanted into the mammalian brain and can continue to express foreign gene (transgene) product. The present example was conducted to determine whether sufficient transgene product can be made by genetically modified cells in vivo to complement or repair an absent or previously damaged brain function.

Construction of NGF Vector pLN.8RNL

A retroviral vector, similar to one described previously (Wolf, et al., *Mol. Biol. Med.* 5:43-59 (1988)), was constructed from Moloney murine leukemia virus (Mo-MuLV) (Varmus et al., *RNA Tumor Viruses*; Weiss et al., Cold Spring Harbor Press, Cold Spring Harbor, N.Y., p. 233 (1982)). The pLN.8RNL vector contains the 777 base pair Hgal-Pstl fragment of mouse NGF cDNA (Scott et al., *Nature* 302; 538 (1983); Ullrich et al., *Nature* 303:821 (1983)), under control of the viral 5' LTR. This insert corresponds to the shorter NGF transcript that predominates in mouse tissue receiving sympathetic innervation (Edwards et al., *Nature* 319:784 (1986)) and is believed to encode the precursor to NGF that is secreted constitutively. The vector also included a dominant selectable marker encoding the neomycin-resistance function of transposon Tn5 (Southern et al., *J. Mol. Appl. Genet.* 1:327 (1982)), under control of an internal Rous sarcoma virus promoter.

The 777 bp Hgal-Pstl fragment was isolated from NGF cDNA from plasmid pSPN15' (Wolf et al., *Mol. Biol. Med.* 5:43-59 (1988)}. Briefly, the N1 vector described by Wolf, supra (supplied by Dr. Breakfield, Harvard Medical School, Harvard, Boston) was cloned into the Pstl site of plasmid pSP64 (Promega, Madison, WI). Plasmid pSPn15' was digested with restriction enzymes Pstl and Hgal using established methods (Maniatis et al., Cold Spring Harbor Press, Cold Spring Harbor, N.Y., (1982) and the 777 basepair DNA fragment containing the NGF sequences was isolated by standard purification methods (Maniatis, et al., supra). The 777 bp fragment was then blunt end ligated into plasmid pLMTPL as described by Yee et al., in *Proc Nat'l. Acad. Sci. (USA)* 84:5197-5201 (1987), incorporated by reference herein and supplied by Drs. Lee and Xu, (University of California, San Diego, Calif.). Plasmid pLMTPL was digested with Hind III to remove the metallothionein promoter and most of the HPRT cDNA, and the overhanging 5' ends were repaired using Klenow polymerase as described by Maniatis et al., supra. The overhanging ends of the 777 bp fragment isolated as above were similarly repaired. The 777 bp fragment was then blunt end ligated into the digested plasmid pLMTPL. The resulting plasmid was called PLN.8L and was transfected into *E. coli* strain DH1, grown and purified by established methods for plasmid purification including cesium chloride centrifugation (Maniatis et al., supra). The purified plasmid pLN.8L was then digested using restriction enzymes BamHl and Clal and the resulting 6.1 kilobase fragment was ligated to a 2.1 kilobase Bamhl-Clal fragment isolated from plasmid pLLRNL.

Figure 8:
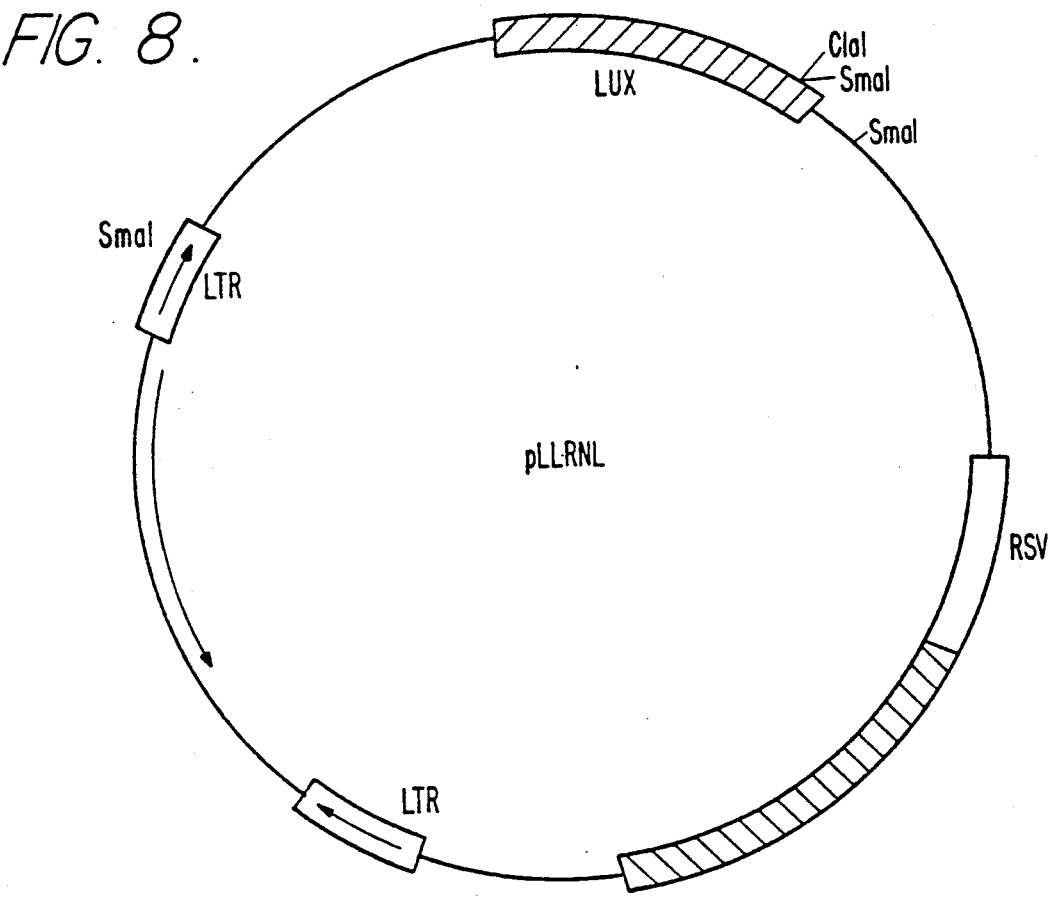

Plasmid pLLRNL was derived from plasmid JD204 described by de Wet et al., in *Mol. Cell. Biol.* 7:725-737 (1987) as follows: A 1717 bp HindIII-Sspl fragment from the firefly luciferase gene derived from plasmid JD204 and a 1321 bp HindIII-Smal fragment of the plasmid pSV2Neo described by Southern and Berg in *Mol. Apcl. Genet.* 1:327-341 (1982) were ligated with a fragment containing a mutated Rous sarcoma virus (RSV) promoter in a 300 bp BamHl-Hind III fragment from plasmid pUCRH. Plasmid pLLRNL is depicted in FIG. 8.

Figure 9:
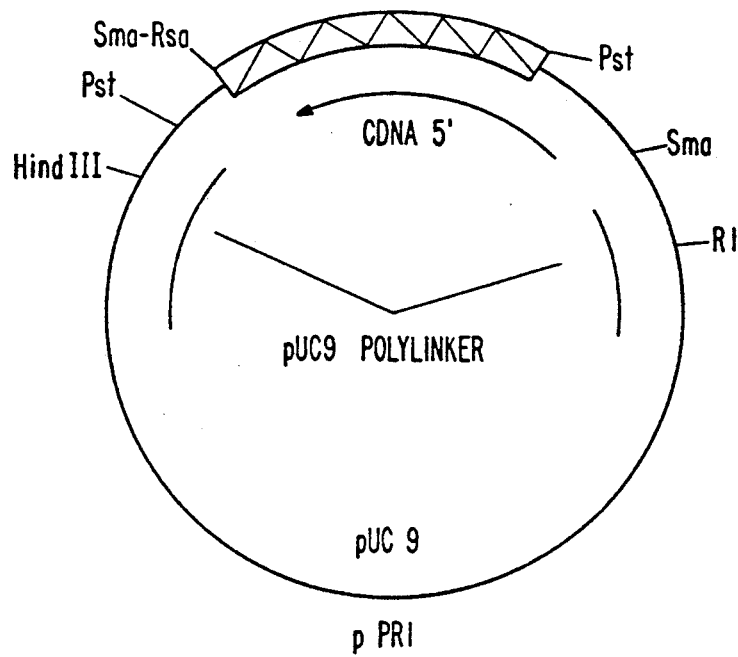

Plasmid pUCRH was produced as follows. Plasmid pRSVneo was restricted using HindIII and the linearized plasmid was ligated with the remaining fragment from plasmid pPRl (FIG. 9) (supplied by Dr. Friedmann, University of California, San Diego, Calif.) obtained by restriction using HindIII to remove HPRT sequences. Plasmid pPRl was obtained from plasmid p4aA8 (Jolly et al., *Proc. Nat'l Acad. Sci.* 80:477-481 (1983)) using Pst and Rsa. The resulting plasmid was called pRHN and was then restricted with PvuII and religated to form plasmids PN(+) and PAC(−). PN(+) was then restricted using BamHl. The resulting linearized plasmid was ligated with a fragment obtained from plasmid pSVori restricted with BamHl. Plasmid pSVori was obtained by restricting plasmid p4aA8 (Jolly et al., *Proc. Nat'l. Acad. Sci.* 80:477-481 (1983)) with Sall and Pstl, and subcloning the resulting fragment into plasmid pUC18 (Bethesda Research Laboratories, Gaithersburg, MD) that had been restricted with Sall and Pstl. The resulting plasmid was termed pSVori.

The plasmid pRH+S+ that resulted from ligation of the BamHl restricted plasmid PN(+) and the BamHl restricted plasmid pSVori was then restricted with MstII and the overhanging 5' ends were repaired using Klenow polymerase as described above. This fragment was ligated with a M13mp18 (Bethesda Research Laboratories) linearized with Smal and phosphatased with calf intestinal alkaline phosphatase (Boehringer Mannheim, Mannheim, W. Germany). The resulting plasmid was called pmpRH and contained the HPRT cDNA expressed from the RSV promoter.

Figure 10:
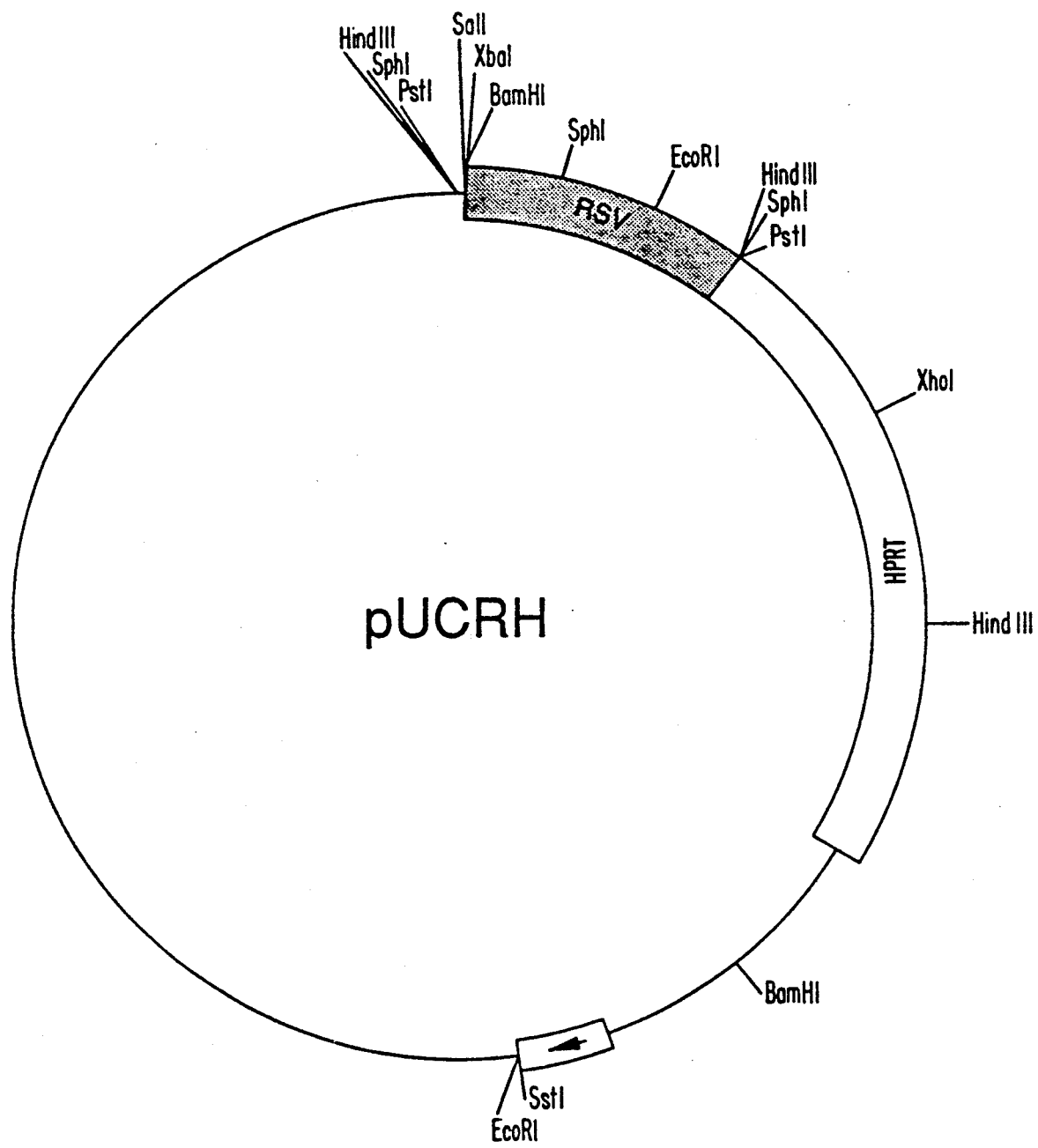

Plasmid pmpRH was subject to site-directed mutagenesis as described by Kunkel et al., *Proc. Nat'l. Acad. Sci. USA* 82:488-492 (1985), incorporated by reference herein in order to alter the polyadenylation signal AATAAA to AGCAAA. After mutagenesis the resulting plasmid was restricted using HindIII and the resulting fragment was ligated to a HindIII fragment from restriction of plasmid pUC19 (Bethesda Research Laboratories) to produce plasmid pUCRSV. Plasmid pUCRSV was restricted using BamHl and Pstl to produce a fragment containing the RSV promoter. This fragment was ligated to a Pstl-Sstl fragment containing the gene encoding HPRT obtained by restriction of the plasmid pLSΔPΔLM as described in Example I, supra and to a BamHl-Sstl fragment obtained from plasmid pUC19, forming plasmid pUCRH (FIG. 10). The product of ligation between the BamHl-HindIII fragment from pUCRH, the 1717 bp HindIII-Sspl fragment from pJD204 and the 1321 bp HindIII-Smal fragment from pSV2Neo was transfected and purified by established methods as described above and termed plasmid pLLRNL (FIG. 8).

Figure 11:
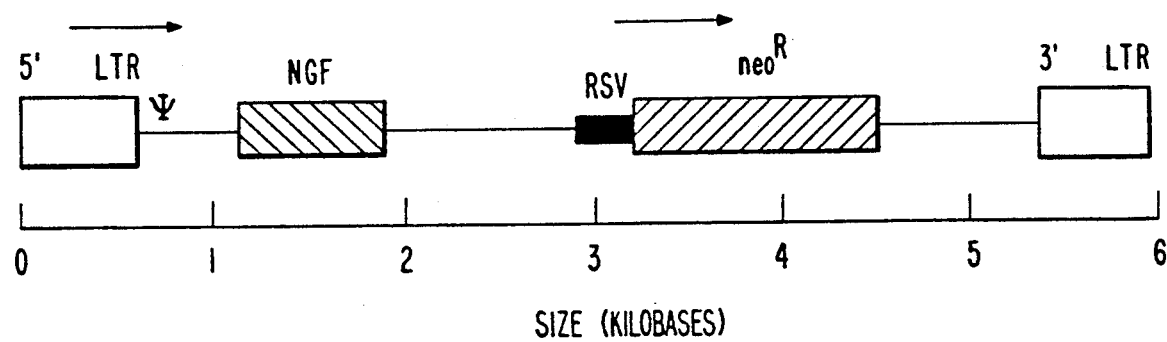
Figure 12:
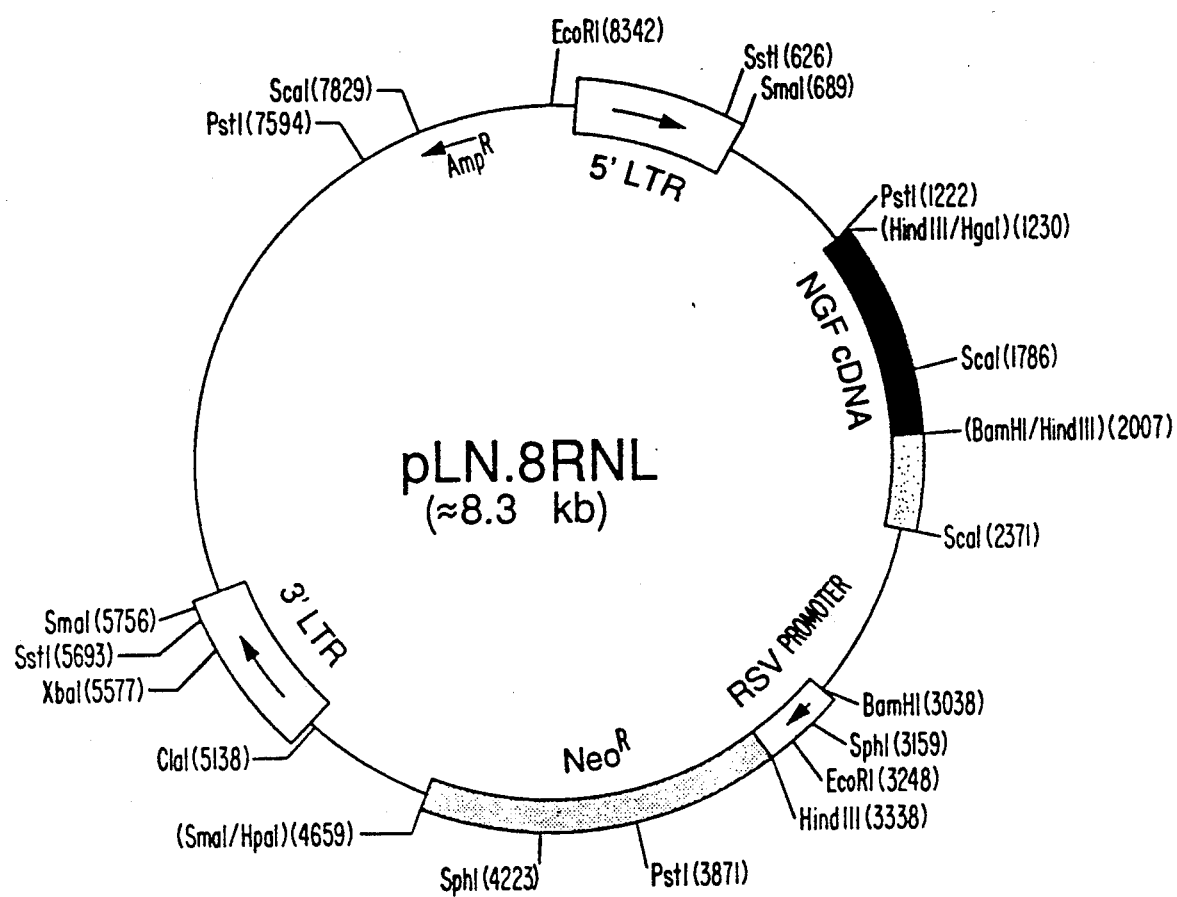

After transfection and purification, the plasmid resulting from ligation of the 6.1 BamHl-Clal kilobase fragment from plasmid pLN.8L and the 2.1 kilobase BamHl-Clal fragment from plasmid pLLRNL was termed pLN.8RNL. (FIGS. 11 and 12).

Preparation of Transmissable Retrovirus

Transmissible retrovirus was produced by transfecting pLN.8RNL into PA317 amphotropic producer cells (Miller et al., *Mol. Cell. Biol.* 6:2895 (1986)), supplied by Dr. Miller, Fred Hutchinson Cancer Research Center, Seattle, WA), by the calcium phosphate co-precipitation method (Graham et al., *Virology* 52:456 (1973)), and using medium from these cells to infect $\psi$-2 ecotropic producer cells (Mann et al., *Cell* 33:153 (1983)) in the presence of 4 $\mu$g/ml Polybrene (Sigma Chemical, St. Louis, MO). Virus from the $\psi$2 clone producing the highest titer, $4 \times 10^5$ colony forming units/ml, was used to infect the established rat fibroblast cell line 208F (Quade, *Virology* 98:461 (1979) as described by Miyanohara et al., in *Proc. Nat'l. Acad. Sci. USA* (1988)).

Assay for NGF Production and Secretion

Individual neomycin-resistant 208F colonies, selected in medium containing the neomycin analog G418, were expanded and tested for NGF production and secretion by a two site (ELISA) enzyme immunoassay (Korsching et al., *Proc. Nat'l. Acad. Sci. (USA)* (80:3513-3516 (1983)), using commercially available reagents according to the manufacturer's protocol (Boehringer Mannheim, Biochemical W. Germany). The clone producing the highest levels of NGF contained 1.7 ng NGF/mg total cellular protein and secreted NGF into the medium at a rate of 50 pg/hr $10^5$ cells. The NGF secreted by this clone was biologically active, as determined by its ability to induce neurite outgrowth from PC12 rat pheochromocytoma cells (Greene, et al., *Proc. Nat'l. Acad. Sci. USA* 73:2424 (1976)). Uninfected 208F cells, in contrast, did not produce detectable levels of NGF in either assay.

Fimbria Fornix Transection

Fimbria fornix transection was performed as described by Gage et al., *Brain Res.* 268:27-37 (1983) and in *Neuroscience* 19(1):241-255 (1986), both of which are incorporated by reference herein. Briefly, adult female Sprague-Dawley rats (Bantin and Kingman, San Francisco, Calif.) weighing between 200 g and 225 g at the beginning of the experiment were used. The animals were anesthetized with intrapertioneal injections of a ketamine-xylazine mixture (10 $\mu$g/kg Ketalar, Parke-Davis Ann Arbor, MI, and 5 $\mu$g/kg Rompun, Hoechst, Frankfurt, W. Germany). Unilateral aspirative lesions were made by suction through the cingulate cortex, completely transecting the fimbria fornix unilaterally, and removing the dorsal tip of the hippocampus as well as the overlying cingulate cortex to inflict a partial denervation on the hippocampus target, as described in Gage et al., *Brain Res.* 268:27-37 (1983). All animals in each of the experimental groups received the same complete unilateral aspirative lesion. Fimbria fornix lesions as described above were made in 16 rats; 8 rats received grafts of infected cells while the remaining 8 received uninfected control cells.

Figure 13C:
Figure 13B:
Figure 13A:

Sections stained for fibronectin, a fibroblast specific marker, revealed robust graft survival that was comparable in both groups (FIG. 13a, FIG. 13b). Sections stained for choline acetyltransferase (ChAT) to evaluate the survival of cholinergic cells bodies indicated a greater number of remaining neurons on the lesioned side of the medial septum in animals that had received grafts of infected cells than in animals that had received control grafts (FIG. 13c-FIG. 13f).

Retrovirus-infected (NGF secreting) and control 208F cells were removed from confluent plates with Dulbecco's phosphate buffered saline (pBS) containing 0.05% trypsin and 1 mM EDTA and taken up by trituration with PBS supplemented with 1 mg/ml glucose, 0.1 mg/ml each MgC12 and CaC12 (complete PBS) and 5% rat serum to inactivate the trypsin. Cells were pelleted by centrifugation at 1000 $\times$g for 4 min. at 4° C., washed twice with complete PBS, and resuspended in complete PBS at 105 cells/$\mu$l. Four $\mu$l of suspended cells were injected free-hand using a Hamilton syringe into the cavity and lateral ventricle ipsilateral to the cavity in the animals. A piece of Gelfoam was gently placed on the surface of the cavity and the animals were sutured.

Immunohistochemistry

At 2 weeks following surgery the rats were perfused and their brains were removed, fixed overnight and placed in phosphate-buffered 30% sucrose for 24 hr at 4° C. Sections 40 $\mu$m thick were cut on a freezing sliding microtome and stored in cryoprotectant (phosphate-buffered glycerol and ethylene glycol) at $-20$° C. Every fifth section was labelled immunohistochemically by standard procedures using polyclonal antibodies to fibronectin to evaluate fibroblast survival. Polyclonal antibodies to choline acetyltransferase (anti-ChAT antiserum) were also generated to evaluate the survival of cholinergic cell bodies as described by Gage et al. in *J. of Comparative Neurol* 269:147-155 (1988), incorporated by reference herein. Tissue sections were processed for immunohistology according to a modification of the avidinbiotin labeling procedure of Hsu et al., 29:1349-1353 (1981), incorporated by reference. This procedure consists of the following steps: 1) overnight incubation with antibody to ChAT or with control antibody (i.e. preimmune serum or absorbed antiserum). The ChAT antibody was diluted 1:1,500 with 0.1 M Tris-saline containing 1% goat serum and 0.25% Trtion X-100; 2) incubation for 1 hr with biotinylated goat antirabbit IgG (Vector Laboratories, Burlingame, Calif.) diluted 1:200 with Tris-saline containing 1% goat serum: 3) 1 hr incubation with ABC complex (Vector Laboratories) diluted 1:100 with Tris-saline containing 1% goat serum;4) treatment for 15 min with 0.05% 3,3'diaminobenzidine (DAB), 0.01% hydrogen peroxide and 0.04% nickel chloride in 0.1 M Tris buffer. Immunolabeled tissue sections were mounted onto glass slides, air dried and covered with Permount and glass coverslips. Two sections stained for ChAT through the septum, 200 $\mu$m apart were used to evaluate the extent of cholinergic cell survival. All the ChAT-positive cells in the ipsilateral septum and in the contralateral septum were counted separatedly and sized for planar area using an Olympus Que-2 image analysis system. Tissues were also stained for acetylcholinesterase (AChE) as described by Hedreen et al., *J. Histochem. Cytochem.* 33:134-140 (1985), incorporated by reference herein, to evaluate the completeness of the fimbria fornix transection.

Figure 14:
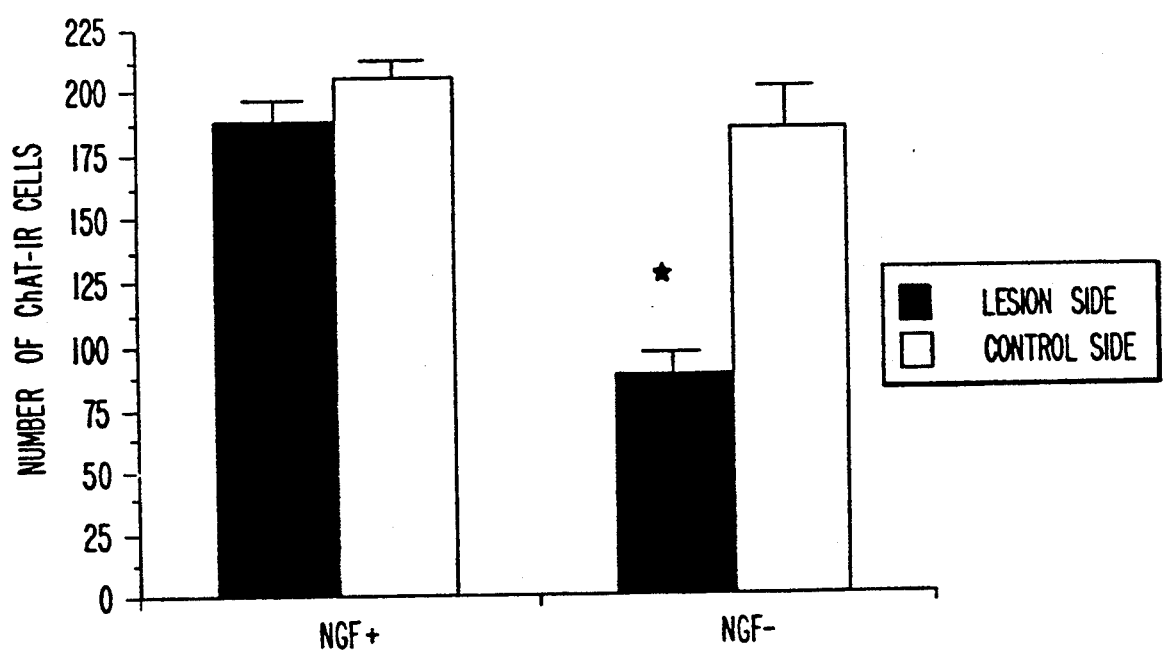
Figures 15A, 15B, 15C:
FIG. 15a–FIG. 15f are photomicrographs of acetylcholinesterase histochemistry as described in Example II, infra (FIG. 15a=low power magnification of an animal grafted with NGF-infected donor cells.
Figure 15F:
Figure 15E:
Figure 15D:
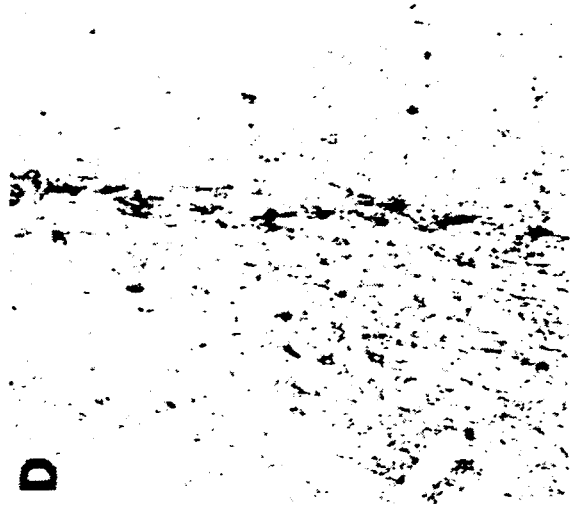

Neuronal survival was quantitated (FIG. 14) and, when expressed as a percentage of the remaining cholinergic cells in the septum ipsilateral to the lesion relative to the intact contralateral septum, was shown to be 92% in animals grafted with NGF-secreting cells but only 49% in animals grafted with control cells. The results from the control group are comparable to previous observations in lesioned animals that had received no grafts (Gage et al., *Neuroscience* 19:241 (1986); Hefti, *J. Neurosci.* 8:2155 (1986); Williams et al., *Proc. Natl. Acad. Sci. USA* 83:9231 (1986); Kromer, *Science* 235:214 (1987); Gage et al., *J. Comp. Neurol.* 369:147 (1988)).

In addition to the significant increase in the percentage of ChAT-positive cells in the NGF group, these animals also showed an increase in acetylcholinesterase (AChE)-positive fiber and cell staining (FIG. 15). Most striking was the observation of a robust sprouting response in the dorsal lateral quadrant of the septum, with the most intense staining abutting the cavity containing the graft. This intense increase in AChE staining was not observed in the group receiving control grafts (FIG. 15).

The above results demonstrate the feasibility of continued transgene expression by cells grafted to the CNS and also present the first demonstration of a phenotypic correction in whole animals brought about by grafted, genetically modified cells.

EXAMPLE III

Grafting of Genetically Modified Fibroblasts Expressing L-DOPA Into The CNS of A Rat Model of Parkinson's Disease This example was undertaken to demonstrate that the methods of the present invention for genetic modification of donor cells and grafting of the cells into the CNS can significantly ameliorate the signs of disease in an animal model, such as a rat model of Parkinson's disease.

The strategy for enabling fibroblasts to produce L-DOPA used in this example is based upon the ability of the enzyme tyrosine hydroxylase (TH) to catalyze the conversion of tyrosine to L-DOPA; the rate-limiting step in catecholamine synthesis. Tetrahydro-biopterine ($H_4$-B), the co-factor for TH is required for TH enzymic activity. Since the brain contains significant levels of biopterin, and fibroblasts can reduce biopterin to $H_4$-biopterin, TH should be active in fibroblasts situated within the brain.

Construction of Retroviral Vector pLTHRNL

Figure 16:
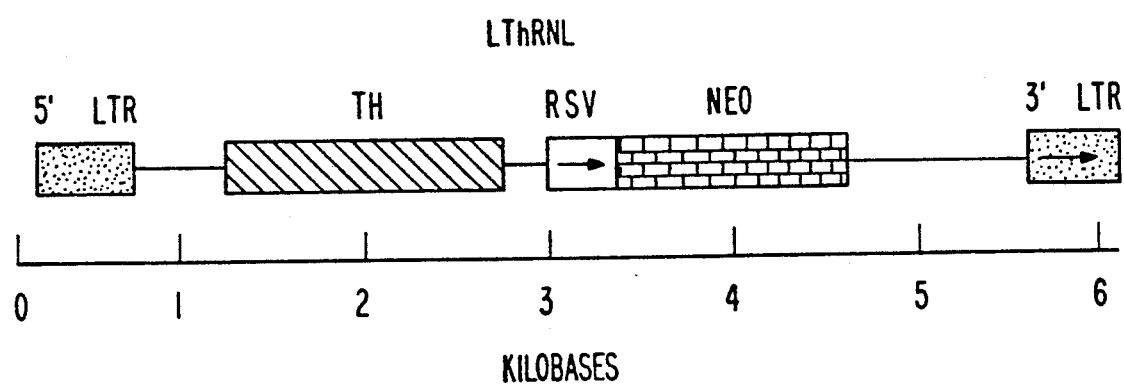

The vector pLTHRNL, a Moloney leukemia virus (Mo-MLV)-derived retroviral vector, was constructed expressing the rat cDNA for tyrosine hydroxylase (TH) from the 5' LTR sequence and contained a neomycin-resistant gene transcribed from an internal RSV promoter (FIG. 16). Fragments from three plasmids: pLRbL, pTH54 and pLHRNL were ligated together to form pLTHRNL. Plasmid pLRbL was obtained by digesting plasmid pLMTPL (obtained as described above in Example II) with the enzymes HindIII and HpaI, and removing the fragment containing the HPRT gene. The remaining plasmid DNA was ligated with the 3.5 kb fragment obtained after restriction of plasmid pGENl-4.5Rb old (pGENl-4.5Rb old was constructed by inserting DNA encoding the retinoblastoma gene (Rb) intoplasmid pGENl, available from Promega, Madison, WI, and was supplied by Dr. Lee, University of California, San Diego, Calif.) using HindIII and Sca2. The resulting plasmid was named pLRbL.

A 1688 bp fragment containing rat TH cDNA was obtained from the plasmid pTH54 (O'Malley, *J. Neurosci. Res.* 60:3-10 (1986), supplied by Dr. O'Malley, Washington University, St. Louis, MO) by digestion with BamH1 and Sph1.

Figure 17:
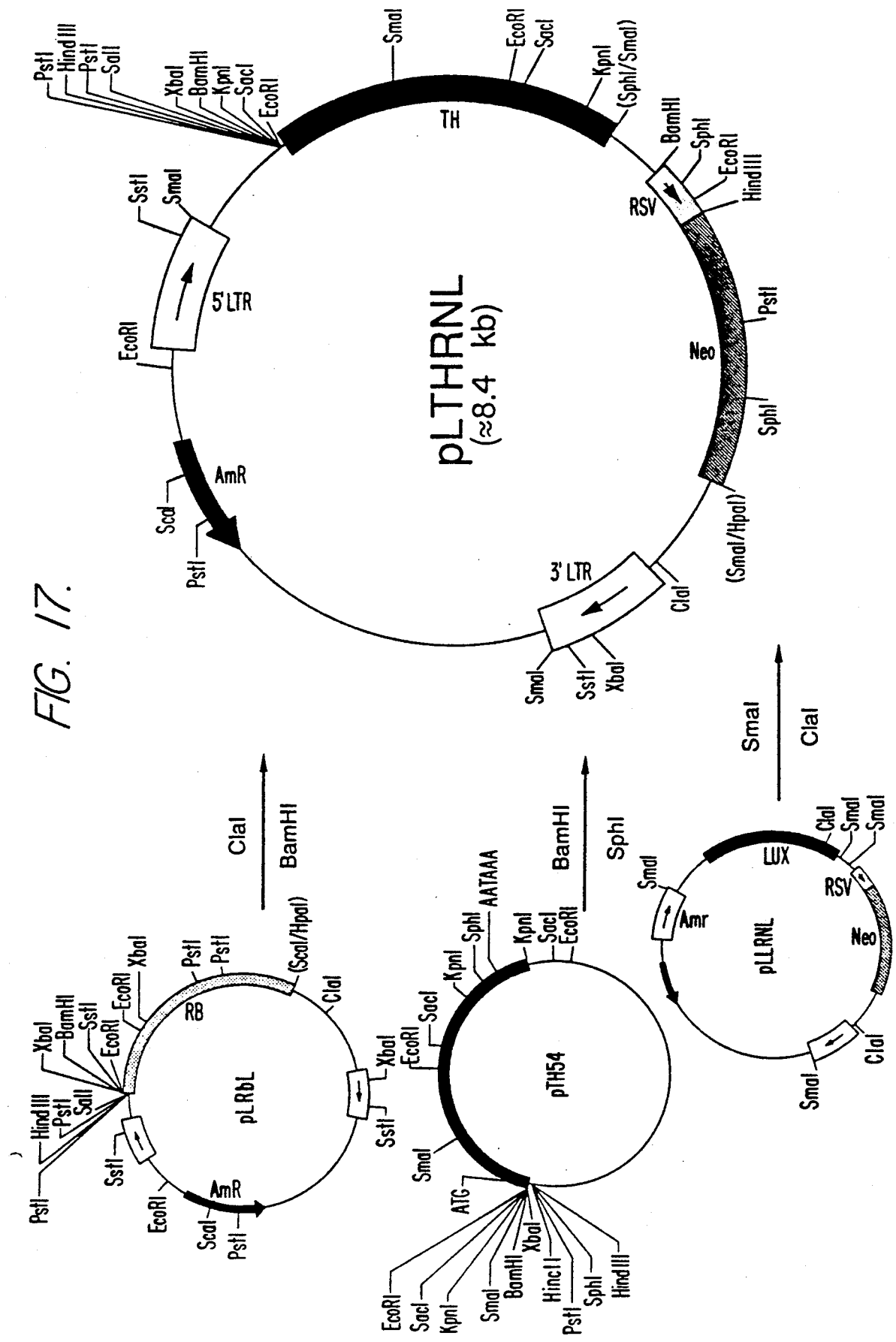
FIG. 17 is a depiction of the derivation of vector pLTHRNL as shown in FIG. 16 and described in Example II, infra.

The fragments from plasmid pTH54 and plasmid pLRbL were ligated with a ClaI and SmaI fragment obtained from plasmid pL2RNL (described above in Example I) to obtain the vector pLTHRNL containing the retroviral provirus for transfection into producer cells to produce virus carrying the gene encoding the enzyme tyrosine hydroxylase. The derivation of and circular restriction map for pLTHRNL is shown in FIG. 17.

Helper-free retrovirus was produced and retroviral infections were done as described in Example II, supra. Plasmid DNA containing the LTHRNL provirus was $CaPO_4$ transfected as described by Wigler et al., *Cell* 11:223-232 (1977), incorporated by reference herein, into the amphotropic PA317 helper line supplied by (Dr. Miller, Fred Hutchinson Cancer Research Center, Seattle, Wash.). Two days post-transfection, media from these cells were filtered and used to infect the ecotropic Ψ2 helper line (Miller et al., *Mol. Cell. Biol.* 6:2895-2902 (1986), supplied by Dr. Miller). A G-418-resistant ψ2 clone (ψ2/TH) that contained the highest level of TH activity and produced the highest titre of virus ($5 \times 10^5$/ml) was selected. Immortalized, rat fibroblasts (208F) (Quade, *Virology* 98:461-465 (1979)) were infected at a multiplicity of infection (MOI) of less than $10^4$ with LTHRNL virus produced by the ψ-2/TH producer cells. G-418 resistant clones were established for further study. All retroviral infections were done in the presence of 4 μg of Polybrene (Sigma) per ml. Cells were selected for expression of the neomycin-resistance gene by growth in 400 μg/ml of G-418.

Assay of Tyrosine Hydroxylase Activity

Confluent 10 cm plates of cells were washed two times with Dulbecco's phosphate buffered saline (PBS) not containing calcium or magnesium chloride and the cells were scraped off the plates. The cells were homogenized in 0.15 ml of ice cold 50 mM Tris/50 mM sodium pyrophosphate/0.2% Trtion X-100, adjusted to pH 8.4 with acetic acid, and were centrifuged at $32,000 \times g$ for 15 min at 2–4° C. The supernatant fraction was used for both TH and protein measurements. TH activity was measured with a decarboxylase-coupled assay essentially as described previously (Iovone et al., *J. Neurochem*, 43: 1359-1368 (1986)), but with $^{14}$C-labelled 20 μM tyrosine, 1 mM 6-methyl-5,6,7,8-tetrahydropterin (6MPH$_4$) (Calbiochem, La Jolla, Calif.), and potassium phosphate buffer (pH 6). Protein was determined by the method of Lowry et al. (*J. Biol. Chem.* 193:265 (1951)) using bovine serum albumin as standard.

Assays of Catecholamines and their Metabolites

Cultured cells were scraped off plates as in the assay of tyrosine hydroxylase activity except ascorbic acid (final concentration of 50 μM) was added to the cell pellets prior to freezing. Cells were grown in DME plus 10% fetal calf serum. Some cultures were supplemented with 0.1 mM 6MPH$_4$ 16 hours prior to harvesting. Cells were homogenized in 250 μl of ice cold 0.1 N $HClO_4$/0.1% sodium metabisulfite/0.2% $Na_2EDTA$ containing 5 ng/ml of 3,4-dihydroxybenzylamine (DHBA) as internal standard. Dopamine DOPA, 3,4-dihydroxyphenylacetic acid (DOPAC), and DHBA were extracted from the supernatant fraction by alumina absorption (Anton et al., *J. Pharmacol. Exc. Ther.* 138:360-375 (1962)) and eluted with 150 μl of 0.1N $H_3PO_4$. They were analyzed by HPLC with electrochemical detection as described by Iovone et al., *Brain Res.* 418:314-324 (1987), with the mobile phase modified to contain a higher concentration of sodium octylsulfate (0.45 mM) and lower pH (2.8). Homovanylac acid (HVA) was analyzed by HPLC. The concentration of catecholamines and metabolites in the media was also determined using a different method, HPLC-EC. The alumina extraction procedure described above was omitted and the media was adjusted to 0.1 perchloric acid acid/0.01M EDTA was centrifuged 10,000 g×10 min to remove precipitated material and used directly for HPLC-EC. In this system, the whole phase consisted of 0.137% SDS in 0.1 M phosphate buffer, pH 3.2 (Buffer A) or 40% methanol in 0.1 M phosphate buffer, pH 3.35 (Buffer B). Compounds in sample were eluted for 12 minutes in 100% Buffer A, followed by a gradient increasing linearly over 30 minutes to 100% Buffer B. The eluant was then passed through a series of 16 coulometric electrodes set at 60 mV increments.

Rat Model of Parkinson's

Female Sprague-Dawley rats received a unilateral injection of 12 μg in 2 μl saline-ascorbate 6-hydroxydopamine (6-OHDA) into the medial forebrain bundle (coordinates: AP=−4.4; ML=1.1; DV=7.5). Completeness of the lesion produced was assessed 10 to 20 days post-injection by either apomorphine (0.1 mg/kg, subcutaneously (s.c.)) or amphetamine (5 mg/kg, s.c.) induced rotational behavior (Ungerstedt and Arbuthnott, *Brain Res.* 24:485-493 (1970)). Prior to transplantation, each animal was tested at least twice on separate days to establish the baseline rotational response to apomorphine or amphetamine for each animal. Animals turning at a rate of more than 7 turns per minute (Schmidt et al., *J. Neurochem.* 38:737-748 (1982)) were included in the study (at least 7 contralateral rotations/min following apomorphine administration and at least 7 ipsilateral rotations/min towards the side of the lesion following amphetamine administration; 19 apomorphine tested, 14 amphetamine tested). The average percent change in the number of rotations from baseline to post-transplantation was compared in the 4 experimental groups of animals.

Grafting of Fibroblasts

Confluent 10 cm plates of cultured TH-infected or noninfected fibroblasts were loosened from the plates in PBS containing 0.05% trypsin and pipetted up in PBS supplemented with 1 mg/ml glucose, 0.1 mg/ml MgCl2 and 0.1 mg/ml CaCl2 (complete PBS) plus 5% rat serum to inactivate the trypsin. The cells were washed twice with complete PBS using centrifugation at 1000×g and were resuspended in complete PBS at a density of 80,000 cells per μl. Since graft placement has been shown to be crucial for recovery from rotational asymmetry (Herrera et al., *Brain Res.* 297:53-61 (1984); Dunnett et al., *Scand. Suppl.* 522:29-37 (1983)), suspended cells were injected stereotaxically into 2 to 3 separate locations within the rostral (coordinates: AP=1.4; ML=2.0; DV=3.5-5.5 to AP=2.5; ML=1.5; DV=3.5/4.5) and caudal areas (AP=0.4; ML=3.0; DV=3.5/4.5) of the denervated caudate. A total of 4 μl were delivered in two equal deposits over a 1 to 2 mm area at each site. Control lesioned animals received injections of noninfected fibroblasts.

Post-Grafting Behavioral Testing

Grafted rats were tested for rotational asymmetry 1 and 2 weeks following fibroblast grafting.

Histological Methods

Following the final behavioral test, rats were deeply anesthetized and perfused with 10% formalin. Brains were postfixed overnight, placed in 30% sucrose for 48 hrs and then sectioned (40 μm) on a freezing microtome. Alternate sections were stained for cresyl violet, fibronectin (FB) or TH using a polyclonal anti-tyrosine hydroxylase antibody (Eugenetech, N.J.). Briefly, the sections were rinsed in Tris-buffered-saline (TBS) solution (pH 7.4) containing 0.25% Trtion-X. The sections were incubated for 24 hrs at 4° C. with rabbit polyclonal antibodies to tyrosine hydroxylase diluted 1:600 or polyclonal anti-fibronectin diluted 1:2000 in TBS containing 0.25% Trtion-X and 3% goat serum. After thorough rinsing, the sections were incubated for 1 hr with biotinylated goat anti-rabbit IgG (Vectastain) diluted 1:200 in 0.1 M TBS containing 0.25% Trtion-X and 1% goat serum, followed by several rinses in TBS containing 0.25% Trtion-X and 1% goat serum. The sections were then incubated for 1 hr at room temperature with a complex of avidin and biotinylated horseradish peroxidase (Vectastain, ABC kit, Vector Labs, Burlingame, Calif.) diluted 1:100 in 0.1 M TBS containing 0.25% Trtion-X and 1% goat serum, followed by thorough rinses. The peroxidase was visualized by reacting with 0.05%, 3,3-diaminobenzidine tetrahydrochloride (DAB) (Sigma Chemical Co., St. Louis, MO) and 0.05% $NiCl_2$ and 0.01% $H_2O_2$ in TBS for 15 min at room temperature. Mounted sections were assessed for size and placement of fibroblast positive grafts.

Establishment of a Fibroblast Clone Expressing High Levels of TH

Immortalized, rat fibroblasts (208F) were infected with LThRNL virus produced by the ψ2/TH producer cells and 12 G-418-resistant clones were established. Table 1 shows the TH activity of 3 of these 12 G-418 resistant clones with the highest TH activity and the TH activity of the ψ2 producer line. The TH activity of the clones with the highest activity (clones 208F/TH-8 and 208F/TH-11) contained approximately a quarter of the TH activity of rat striatum. The 208F/TH-8 clone that contained the highest TH activity, was chosen for further study.

TABLE 1

| TH Activity of Cell and Tissue Extracts | |
|---|---|
| Cell Line | TH Activity* |
| ψ2/TH | 1.7 |
| 208F/TH-8 | 2.9 |
| 208F/TH-11 | 2.6 |
| 208F/TH-9 | 0.4 |
| 208F/CONTROL | 0.0 |
| Rat Striatum | 9.8 |

*TH activity is expressed in units of pmoles DOPA/min/mg protein

Fibroblasts Expressing TH Produce and Secrete L-DOPA.

Cell extracts from the 208/TH-8 fibroblasts expressing TH and control 208F fibroblasts were assayed for L-DOPA (Table 2). Only 287F/TH-8 cells cultured in media supplemented with 6MPH4 produced L-DOPA. Control cells did not contain any detectable amounts of L-DOPA. Dopamine and its metabolites DOPA and HVA were below detectable levels in both 208F/TH-8 and 208F/control cells.

TABLE 2

L-DOPA Concentration of Cell Extracts and Media

| | L-DOPA Concentration[1] | | | |
|---|---|---|---|---|
| | Cell Extract | | Cell Media | |
| Cell Clone | no 6MPH4[2] | +6MPH4[3] | no 6MPH4[2] | +6MPTH4[3] |
| 208F/CONTROL | <0.25 | <0.25 | N.D.[4] | 63 |
| 208F/TH-8 | <0.25 | 1.38 | N.D. | 239 |

[1]L-DOPA concentration is expressed in units of nanograms (ng)/mg protein for cell extracts and in units of ng/hr/$10^6$ cells for cell media.
[2]Cell incubated in normal media.
[3]Cells incubated overnight in normal media supplemented with 0.1 mN DL-6-Methyl-5,6,7,8-tetrahydropterin.
[4]N.D. not determined As shown in Table 2, L-DOPA was also detected in the media of the 208F/TH-8 cells: 63 ng/hr per $10^6$ cells in control 208F media and 239 ng/hr per $10^6$ cells in TH-infected media. There was no detectable DOPA, DA, MHPG or HVA in the media.

Histologic Examination of Grafts

Figure 18A:
FIGS. 18a–FIG. 18d are photomicrographs of fibroblast grafts to the caudate showing fibronectin immunoreactivity as described in Example III, infra (magnification.
Figure 18B:
Figure 18C:
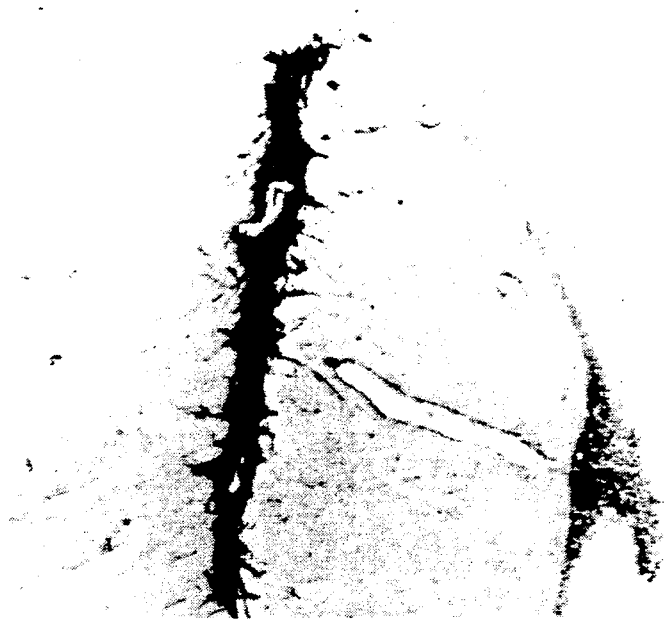
Figure 18D:

Fibroblast grafts survived intraparenchymal transplantation to many areas within denervated caudate. Surviving fibronectin positive grafts were typically moderate to large in size regardless of placement (FIG. 18a and b). Only 4 out of 31 grafts were classified as non-surviving based on the confinement of fibronectin staining to the syringe tract (FIG. 18c and d). Behavioral data from the rats with nonsurviving grafts were excluded from statistical analyses. TH immunoreactivity was not observed in the fibroblasts either in vitro or in vivo.

Effect of Grafts on Rotational Asymmetry

The number of drug-induced rotations for each individual animal were compared before and 2 weeks after transplantation. Rotational scores from rats tested with apomorphine were pooled with those from rats tested with amphetamine since no difference was seen between these groups.

Figure 19:
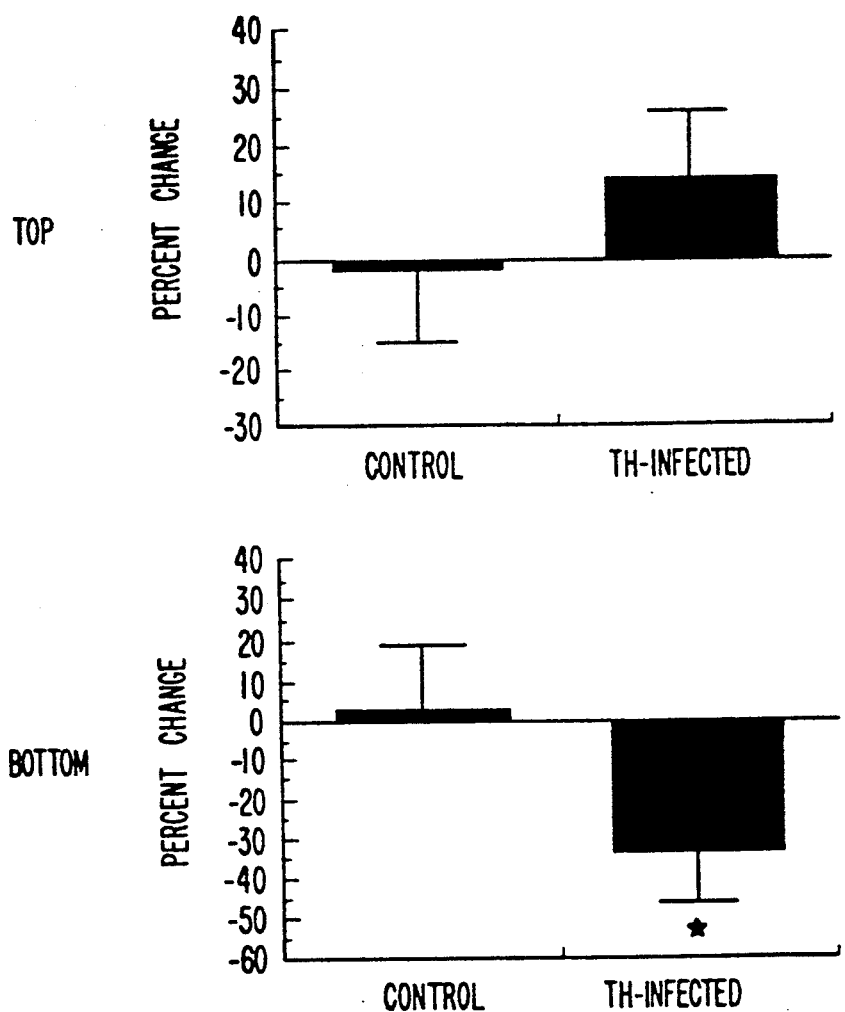
FIG. 19 is a graph showing the average percent change in the number of rotations from baseline to post-transplantation in 4 experimental groups of animals as described in Example III, infra (Top of figure: placement of control and TH-infected grafts in caudal striatum; Bottom: placement of control and TH-infected grafts in rostral striatum; bars indicate standard deviation).
Figure 19:
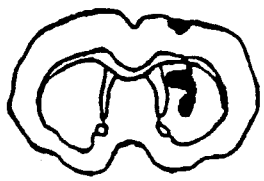
Figure 19:
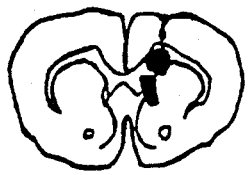

Amelioration of rotational asymmetry was dependent on graft placement. Rats with fibroblast grafts confined to cauda striatum (FIG. 19 Top) (AP=0 to 0.4) had no significant changes in rotational behavior. Rats which had surviving TH-infected fibroblasts in rostral caudate striatum (AP=1.4 to 2.2) showed an average 33% reduction in drug-induced rotations 2 weeks following transplantation (FIG. 19 Bottom).

These results demonstrate that the rat cDNA coding for the TH gene can express functional TH enzymic activity when stably transduced into fibroblasts. Fibroblasts expressing the TH gene can produce and secrete L-DOPA in vitro. When these DOPA-producing fibroblasts were implanted into the rostral caudate region, they substantially and significantly reduce the rotational asymmetry in the rat model of Parkinson's. Since control fibroblasts do not produce detectable levels of L-DOPA in vitro and do not attenuate the rotational asymmetry of these rats, the ability of these DOPA-producing cells to attenuate these rat's rotational symmetry must be due solely to the presence of the TH gene within the cells. These data demonstrated an effect on rotational behavior for at least two weeks, since we wanted to correlate rotational behavior with histologic analysis.

The effect of the DOPA-producing fibroblasts on rotational behavior were dependent on placement in the rostral caudate. Previous data utilizing fetal neuronal grafts into rats have shown that attenuation of rotational asymmetry is best achieved when the grafts are placed into the rostral caudate, Dunnett. Since the fibroblasts used cannot sprout axons, the location of the graft is even more critically dependant upon proper graft placement.

The exact mechanism by which the DOPA-producing fibroblasts reduce rotational asymmetry remains to be determined. Presumably, once L-DOPA is secreted, there remains enough caudate DOPA decarboxylase activity, even within these totally denervated animals (Lloyd et al., Science 170:1212–1213 (1970); Hornykiewicz, British Med. J. 29:172–178 (1973)), to convert L-DOPA to dopamine that then modifies drug-induced rotational behavior. This postulated mechanism of action of these DOPA-producing cells would be consistent with the well established efficacy of systemic L-DOPA therapy for Parkinson's disease (Calne, N. Eng. J. Med. 310:523–524 (1984)). These DOPA-producing fibroblasts are in effect small localized pumps of L-DOPA.

The ability, demonstrated in this example, to modify cells to produce L-DOPA broadens the search for the ideal type of cell for transplantation therapy of Parkinson's. Any cell that can be genetically-modified to express the TH gene and that can survive long-term in the brain without forming a tumor or causing other damage, may be used. Although these particular immortalized rat fibroblasts have not formed tumors for up to three months, primary cells such as primary fibroblasts or primary glial cells may offer the theoretical advantage of decreased propensity for tumor formation. In addition, the use of the patients own primary cells for an autologous graft would decrease the chance of graft rejection. However, the use of immortalized cells such as the 208F cells used in this example, does offer the advantage of having large amounts of well-characterized cells readily available.

These results demonstrate that a fibroblast can be genetically-modified to supply a function normally supplied by a neuron, therefore not requiring the use of fetal tissue for neuronal transplantation. The ability to combine transplantation modalities with gene-transfer presents a powerful method for the treatment of CNS dysfunction. The methods of the present invention may thus be used for treatment of other models of animal and human brain disease.

It is apparent that many modifications and variations of this invention as set forth above may be made without departing from the spirit and scope of the present invention. The specific embodiments described are given by way of example only and the invention is limited only by the terms of the appended claims.

We claim:

1. A method for treating defective, diseased or damaged cells in the mammalian central nervous system comprising grafting donor cell from the same mammalian species into the central nervous system, said donor cells genetically modified to produce a functional molecule in a sufficient amount to ameliorate said defective, diseased or damaged cells in the central nervous system.

2. The method of claim 1 wherein the step of grafting said donor cells comprises introducing said donor cells into the brain of a subject.

3. The method of claim 1 wherein the step of grafting said donor cells comprises introducing said donor cells into the spinal cord of a subject.

4. The method of claim 2 or 3 wherein said introducing comprises in tracerebral, intraventricular, subdural space or intravenous injection.

5. The method of claim 1 wherein said donor cells are modified by insertion of a therapeutic transgene into said cells.

6. The method of claim 5 wherein said step of insertion comprises inserting a vector carrying said transgene, wherein said vector is a viral vector.

7. The method of claim 1 wherein said vector is herpes virus vector.

8. The method of claim 6 wherein said vector is a retroviral vector.

9. The method of claim 8 wherein said retroviral vector is the retroviral vector pLN.8RNL having a final construction as shown in FIG. 12.

10. The method of claim 8 wherein said retroviral vector is the retroviral vector pLTHRNL having a final construction as shown in FIG. 16.

11. The method of claim 5 wherein said step of insertion into donor cells comprises nonviral physical transfection of DNA encoding a transgene.

12. The method of claim 11 wherein said nonviral physical transfection comprises microinjection of DNA encoding a transgene.

13. The method of claim 5 wherein said step of insertion into donor cells comprises electroporation.

14. The method of claim 5 wherein said step of insertion into donor cells comprises chemically mediated transfection.

15. The method of claim 14 wherein said chemically mediated transfections comprises calcium phosphate transfection.

16. The method of claim 5 wherein said step of insertion into donor cells comprises liposomal mediated transfection.

17. The method of claim 1 wherein said molecule is selected from the group consisting of growth factors, enzymes, gangliosides, antibiotics, neurotransmitters, neurohormones, toxins, neurite promoting molecules, anti-metabolites and precursors of said molecules.

18. The method of claim 17 wherein said molecule is nerve growth factor.

19. The method of claim 17 wherein said molecule is tyrosine hydroxylase.

20. The method of claim 17 wherein said molecule is L-DOPA.

21. The method of claim 1 further comprising co-administration of a therapeutic agent for treating said disease or damage to the central nervous system.

22. The method of claim 21 wherein said therapeutic agent is selected from the group consisting of growth factors, gangliosides, antibiotics, neurotransmitlers, neurohormones, toxins, antimetabolites, neurite promoting molecules and precursors of these agents.

23. The method of claim 21 wherein said therapeutic agent is cellular matter.

24. The method of claim 23 wherein said cellular matter is selected from the group consisting of adrenal chromaffin cells, fetal brain tissue cells and placental cells.

25. The method of claim 1 further comprising implanting material to the site of said damage or disease, material to facilitate reconnection or ameliorative interactions of injured neurons.

26. The method of claim 25 wherein said material is selected from the group consisting of homogenate of brain, homogenate of placenta, whole cells, synthetic material, neurite promoting extracellular matrix, and genetically modified donor cells.

27. The method of claim 1 wherein said donor cells are selected from the group consisting of fibroblasts, neurons, glial cells, keratinocytes, hepatocytes, ependymal cells and chromaffin cells.

* * * * *

UNITED STATES PATENT AND TRADEMARK OFFICE
CERTIFICATE OF CORRECTION

PATENT NO. : 5,082,670

DATED : January 21, 1992

INVENTOR(S) : Fred H. Gage, Michael B. Rosenberg, Theodore Friedman, and John A. Wolff It is certified that error appears in the above-identified patent and that said Letters Patent is hereby corrected as shown below:

On the title page: Item [54] and Column 1, line 3,

In the Title, after "DISEASE OR DAMAGE" add --OF-- and delete "OR".

Item [75]
In the Inventorship, add John A. Wolff, Madison, Wisconsin.

In the section entitled "OTHER PUBLICATIONS," lines 1 and 2, please change "Gape et al." to --Gage et al.--.

Signed and Sealed this

Twenty-sixth Day of October, 1993

*Attest:*

BRUCE LEHMAN

*Attesting Officer*     *Commissioner of Patents and Trademarks*